United States Patent
Tajima et al.

(10) Patent No.: US 6,589,969 B1
(45) Date of Patent: Jul. 8, 2003

(54) CARBOXYLIC ACID DERIVATIVES AND DRUGS CONTAINING THE SAME AS THE ACTIVE INGREDIENT

(75) Inventors: Hisao Tajima, Osaka (JP); Yoshisuke Nakayama, Osaka (JP); Daikichi Fukushima, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/807,305

(22) PCT Filed: Aug. 9, 1999

(86) PCT No.: PCT/JP99/04868
§ 371 (c)(1),
(2), (4) Date: Apr. 11, 2001

(87) PCT Pub. No.: WO00/23442
PCT Pub. Date: Apr. 27, 2000

(30) Foreign Application Priority Data

Oct. 16, 1998 (JP) .............................. 10-294353

(51) Int. Cl.$^7$ ................... C07D 413/14; A61K 31/42
(52) U.S. Cl. ................. 514/374; 514/369; 514/376; 548/182; 548/204; 548/225; 548/236
(58) Field of Search ................. 548/225, 236, 548/182; 514/369, 374, 376

(56) References Cited

FOREIGN PATENT DOCUMENTS

| JP | 08-325250 | 10/1996 |
| JP | 08-325264 | 10/1996 |
| WO | WO 91/19702 | 12/1991 |
| WO | WO 98/00137 | 1/1998 |

OTHER PUBLICATIONS

Hisashi Shinkai, et al, Isoxazolidine–3,5–dione and Non-cyclic 1,3–Dicarbonyl Compounds as Hypoglycemic Agents, J.Med.Chem. 1998, 41, 1927–1933.
Bernard Hulin, et al, "Hypoglycemic Activity of a Series of α–Alkylthio and αAlkoxy Carboxylic Acids Related to Ciglitazone", J.Med.Chem.., 1996, 39, 3897–3907.

*Primary Examiner*—Joseph K. McKane
*Assistant Examiner*—Kamal Saeed
(74) *Attorney, Agent, or Firm*—Sughrue Mion, PLLC

(57) ABSTRACT

A peroxisome proliferator activated receptor regulator containing a compound of formula (I)

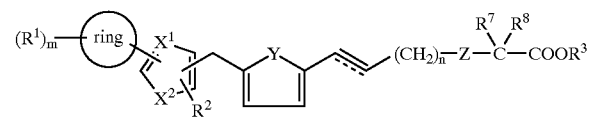

(wherein all symbols are as defined in the specification), or a salt thereof as active ingredient.

Because of having an effect of regulating PPAR, a compound of formula (I) is useful as a hypoglycemic agent, a hypolipidemic agent, a preventive and/or a remedy for diseases associating metabolic disorders (diabetes, obesity, syndrome X, hypercholesterolemia, hyperlipoproteinemia, etc.), hyperlipemia, atherosclerosis, hypertension, circulatory diseases, overeating, coronary heart diseases, etc., an HDL cholesterol-elevating agent, an LDL cholesterol and/or VLDL cholesterol-lowering agent and a drug for relief from risk factors of diabetes or syndrome X.

6 Claims, No Drawings

SEQUENCE LISTING

<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Enhancer sequence including Gal4 protein
      response sequence

<400> SEQUENCE: 1
tcgacggagt actgtcctcc gcgacggagt actgtcctcc gcgacggagt actgtcctcc    60
gcgacggagt actgtcctcc gagct                                          85

<210> SEQ ID NO 2
<211> LENGTH: 9
<212> TYPE: PRT
<213> ORGANISM: Unknown
<220> FEATURE:
<223> OTHER INFORMATION: Nuclear localization signal derived from SV40
      T-antigen

<400> SEQUENCE: 2

Ala Pro Lys Lys Lys Arg Lys Val Gly
1               5

<210> SEQ ID NO 3
<211> LENGTH: 9
<212> TYPE: PRT
<213> ORGANISM: Influenza virus
<220> FEATURE:
<221> NAME/KEY: misc_feature
<223> OTHER INFORMATION: hemagglutinin epitope

<400> SEQUENCE: 3

Tyr Pro Tyr Asp Val Pro Asp Tyr Ala
1               5

CARBOXYLIC ACID DERIVATIVES AND DRUGS CONTAINING THE SAME AS THE ACTIVE INGREDIENT

This application is a 371 of PCT/JP99/04868 filed Aug. 9, 1999.

TECHNICAL FIELD

The present invention relates to a carboxylic acid derivative and a peroxisome proliferator activated receptor regulator containing carboxylic acid derivative as active ingredient.

More particularly, the present invention relates to a compound of formula (I)

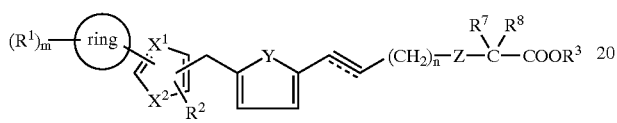

(wherein all symbols are the same meanings as hereinafter described), a non-toxic salt thereof and a hydrate thereof, a process for the preparation thereof and a peroxisome proliferator activated regulator containing thereof as active ingredient.

BACKGROUND

Recently in the study of transcription factors concerned with marker genes expression in adipocytes differentiation, peroxisome proliferator activated receptor (abbreviated as PPAR hereinafter), which is one of intranuclear receptors, has been focused. cDNAs of PPAR were cloned from various kinds of animals, and plural isoform genes were found, particularly in mammals three types of isoforms (α,δ,γ) are known (see J. Steroid Biochem. Molec. Biol., 51, 157 (1994); Gene Expression,. 4, 281 (1995); Biochem Biophys. Res. Commun., 224, 431 (1996); Mol. Endocrinology., 6, 1634 (1992)). PPARγ isoform is predominantly expressed in adipose tissues, immune cells, adrenal gland, spleen, small intestine. PPARα isoform is mainly expressed in adipose tissue, liver, retina, and PPARδ isoform is widely expressed without specificity for tissue (see Endocrinology., 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

pioglitazone

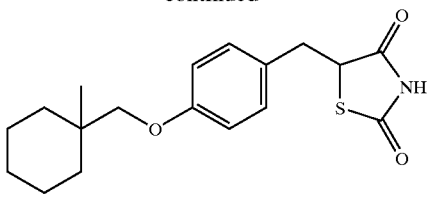

ciglitazone

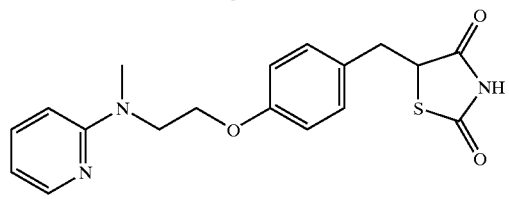

BRL49653

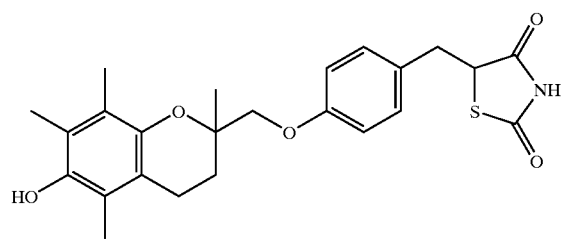

troglitazone

One of the target proteins in the cells of these thiazolidine derivatives is exactly PPARγ and it is resolved that they enhance the transcription activity of PPARγ (see Endocrinology., 137, 4189 (1996); Cell., 83, 803 (1995); Cell., 83, 813 (1995); J. Biol. Chem., 270, 12953 (1995)). Therefore, a PPARγ activator (agonist) which enhances its transcription activity is thought to be hopeful as a hypoglycemic agent and/or a hypolipidemic agent. Furthermore, since a PPARγ agonist is known to promote the expression of PPARγ protein itself (Genes & Development., 10, 974 (1996)), an agent which increases the expression of PPARγ protein itself as well as PPARγ activating agent is also thought to be clinically useful.

Among all of nuclear receptors, PPARγ is related to adipocytes differentiation (see J. Biol. Chem., 272, 5637 (1997) and Cell., 83, 803 (1995)). It is known that thiazolidine derivatives which activate this receptor promote adipocytes differentiation. Recently it was reported that thiazolidine derivatives increase fat mass and cause man to gain weight and to become obese (see Lancet., 349, 952 (1997)). Therefore, it is also thought that antagonists which inhibit PPARγ activity and agents that decrease the expression of PPARγ protein itself are also clinically applicable. On the other hand, a compound that phosphorylates PPARγ protein and decreases its activity is reported (Science., 274, 2100 (1996)). This implies that an agent which does not bind on PPARγ protein as a ligand, but inhibits its activity is also clinically applicable.

From these, PPARγ activators (agonists) and PPARγ regulators for its expression that can increase the expression of the protein itself are expected to be useful as hypoglycemic agents, hypolipidemic agents, and agents for prevention and/or treatment of diseases associated with metabolic disorders such as diabetes, obesity, syndrome X, hypercholesterolemia and hyperlipoproteinemia etc., hyperlipidemia, atherosclerosis, hypertension, circulatory diseases and overeating etc.

On the other hand, antagonists that inhibit the transcription activity of PPARγ or PPARγ regulators that inhibit the expression of the protein itself are expected to be useful as hypoglycemic agents and agents for prevention and/or treatment of diseases associated with metabolic disorders such as diabetes, obesity and syndrome X etc., hyperlipidemia, atherosclerosis, hypertension and overeating etc.

The following fibrate compound (e.g. chlofibrate) is known as a hypolipidemic agent.

chlofibtate

And, it is also resolved that one of the target proteins in the cells of fibrate compounds is PPARα (See Nature., 347, 645 (1990); J. Steroid Biochem. Molec. Biol., 51, 157 (1994); Biochemistry., 32, 5598 (1993)). From these facts, PPARα regulators which can be activated by fibrate compounds are thought to have a hypolipidemic effect, and so they are expected to be useful as agents for prevention and/or treatment of hyperlipidemia etc.

Besides, it has been recently reported that PPARα possesses anti-obese activity in the specification of WO 9736579. In addition, it was reported that the elevation of high density lipoprotein (HDL) cholesterol level and the reduction of low density lipoprotein (LDL) cholesterol, very low density lipoprotein (VLDL) cholesterol and triglyceride levels were induced by activation of PPARα (J. Lipid Res., 39, 17 (1998)). It was also reported that composition of fatty acids in blood, hypertension and insulin resistance were improved by administration of bezafibrate which is one of fibtrate compounds (Diabetes., 46, 348 (1997)).

Therefore, agonists that activate PPARα and PPARα regulators that promote expression of PPARα protein itself are useful as hypolipidemic agents and agents for treatment of hyperlipidemia, and are expected to have HDL cholesterol level-elevating effect, LDL cholesterol and/or VLDL cholesterol levels-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of ischemic coronary diseases.

On the other hand, few reports are found on ligands that activate PPARδ significantly or on biological activities associated with PPAR δ. PPARδ is sometimes called PPARβ, or it is also called NUC1 in human. Until now, as for activity of PPARδ, it is disclosed in the specification of WO 9601430 that hNUC1B (PPAR subtype whose structure is different from that of human NUC1 in one amino acid) inhibited the transcription activities of human PPARα and thyroid hormone receptor. Recently in the specification of WO 9728149, it was reported that the compounds, which possessed high affinity to PPARδ protein and which could activate PPARδ significantly (i.e. agonists) were found out and that they had HDL (high density lipoprotein) cholesterol level-elevating activity. Therefore, agonists that can activate PPARδ are expected to have HDL cholesterol level-elevating effect, and so they are expected to be useful for the inhibition on the progress of atherosclerosis and treatment thereof, as hypolipidemic agents and hypoglycemic agents, for the treatment of hyperlipidemia, as hypoglycemic agents, for the treatment of diabetes, for the relief from risk factor of syndrome X, and for the prevention of occurrence of ischemic coronary diseases.

As for PPAR regulators, the following compounds were reported besides the above-mentioned thiazolidine derivatives and fibrate compounds.

For example, in WO9731907, it is disclosed that the compounds of formula (A)

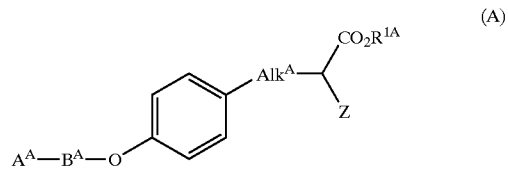

(wherein $A^A$ is phenyl, in which the said phenyl may be substituted with one or more substituent(s) selected from group consisting of halogen, C1–6 alkyl, C1–3 alkoxy, C1–3 fluoroalkoxy, nitrile or —$NR^{7A}R^{8A}$ ($R^{7A}$ and $R^{8A}$ each independently, is hydrogen or C1–3 alkyl);

$B^A$ is (5- or 6-membered heterocyclic ring containing at least one hetero atom selected from O, N and S)—C1–6 alkylene-, in which the said heterocyclic ring may be substituted with C1–3 alkyl;

$Alk^A$ is C1–3 alkylene;

$R^{1A}$ is hydrogen or C1–3 alkyl;

$Z^A$ is —(C1–3 alkylene)phenyl or —$NR^{3A}R^{4A}$)

or pharmaceutically acceptable salts thereof possess PPAR γ agonist activity (the necessary parts in explanation of symbols are shown).

On the other hand, in JP-A-9-323982, it is disclosed that the propionic acid derivatives of formula (B)

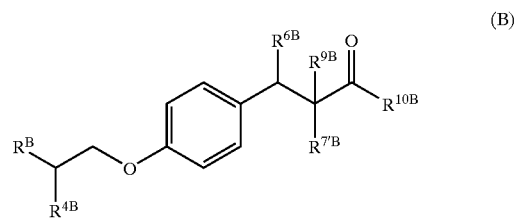

(wherein $R^B$ is

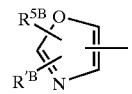

or

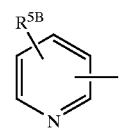

(wherein $R'^B$ is substituted or unsubstituted aromatic hydrocarbon, substituted or unsubstituted aliphatic hydrocarbon ring, substituted or unsubstituted heterocyclic ring or substituted or unsubstituted condensed heterocyclic ring, $R^{5B}$ is lower alkyl), $R^{4B}$ is hydrogen or lower alkyl, $R^{6B}$ is hydrogen or $R^{6B}$ and $R^{9B}$ taken together form double bond, $R^{7B}$ is hydrogen, hydroxy, carboxy, acyl, substituted or unsubstituted alkoxycarbonyl, substituted or unsubstituted lower alkyl, substituted or unsubstituted carbamoyl, substituted or unsubstituted aryloxycarbonyl, substituted or unsubstituted aralkyloxycarbonyl or —$Y^B$—$R^{8B}$ (in which $Y^B$ is —NH— or O, $R^{8B}$ is substituted or unsubstituted acyl, substituted or unsubstituted alkoxycarbonyl, aryloxycarbonyl or aralkyloxycarbonyl), $R^{9B}$ is hydrogen, substituted or unsubstituted lower alkyl or substituted or unsubstituted lower alkoxycarbonyl, $R^{10B}$ is hydroxy, substituted or unsubstituted amino, substituted or unsubstituted lower alkoxy, substituted or unsubstituted lower alkyl, substituted or unsubstituted aryloxy or substituted or unsubstituted aralkyloxy)
or pharmaceutically acceptable salts thereof possess hypoglycemic action and hypolipidemic action. In addition, JP-A-8-325264, JP-A-8-325250, WO9638415 and WO9800137 have also disclosed that analogous compounds possess hypoglycemic action and hypolipidemic action.

In JP-A-5-507920, it is disclosed that the compound of formula (C)

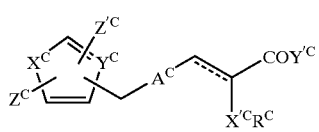
(C)

(wherein $A^c$ is

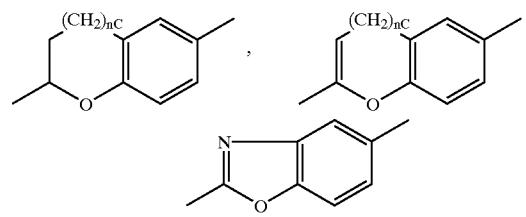
or nC is 0 or 1;
------
represents bond or not represents bond,
$R^C$ is C1~C8 alkyl, C3~C7 cycloalkyl, C3~C8 alkenyl, C3~C8 alkynyl, phenyl,
C7~C8 phenylalkyl, C2~C8 alkanoyl, or one of above groups substituted by one or two of C1~C3 alkyl, trifluoromethyl, hydroxy, C1~C3 alkoxy, fluoride or chloride;
$X^C$ is S, O, $NR^{2C}$, —CH=CH—, —CH=N— or —N=CH;
$R^{2C}$ is hydrogen, C1~C3 alkyl, pheny or benzyl;
$Y^C$ is CH or N;
$Z^C$ is hydrogen, C1~C7 alkyl, C3~C7 cycloalkyl, phenyl, or phenyl substituted by one or two of C1~C3 alkyl, trifluoromethyl, C1~C3 alkoxy, phenyl, phenoxy, benzyl, benzyloxy, fluoride or chloride;
$X'^C$ is O, S, SO or $SO_2$;
$Y'^C$ is hydroxy, C1~C3 alkoxy;
$Z'^C$ is hydrogen or C1~C3 alkyl.) possess hypoglycemic action and hypolipidemic action.

J. Med. Chem., 39, 3897 (1996) have also disclosed that analogous compounds possess hypoglycemic action and hypolipidemic action, the compound of formula (D) is disclosed.

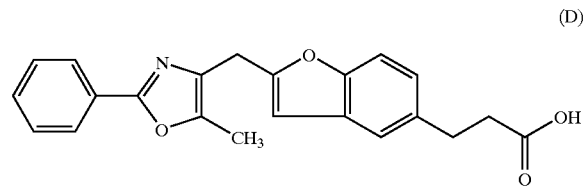
(D)

DISCLOSURE OF THE INVENTION

As the result of energetic investigations in order to find compounds possessing regulating action on PPAR, the present inventors have found that the purpose has been accomplished by the compound of formula (I) and have completed the present invention.

The present invention relates to
(1) a compound of formula (I)

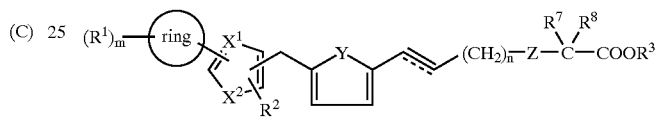
(I)

(wherein $R^1$ independently, is hydrogen, C1~8 alkyl, halogen, C1~4 alkoxy, C1~4 alkoxy, C1~4 alkylthio, nitro, $NR^4R^5$ (in which $R^4$ and $R^5$ each independently, is C1~4 alkyl.), cyano, trifluoromethyl, trifluoromethyloxy, carbocyclic ring or hetero ring (carbocyclic ring and hetero ring are optionally substituted by group selected from C1~4 alkyl, C1~4 alkoxy, halogen or trifluoromethyl.),
$R^2$ is hydrogen, C1~8 alkyl, halogen, C1~4 alkoxy, C1~4 alkylthio, nitro,
$NR^4R^5$ (in which $R^4$ and $R^5$ each independently, is C1~alkyl.), cyano, trifluoromethyl or trifluoromethyloxy,
$R^3$ is hydrogen or C1~4 alkyl,
$X^1$ is —N— or —CH—,
$X^2$ and Y each independently, is —O—, —S— or —$NR^6$— (in which $R^6$ is hydrogen or C1~4 alkyl.),
Z is —O— or —S(O)$_p$— (in which p is 0, 1 or 2),
$R^7$ and $R^8$ each independently, is hydrogen or C1~4 alkyl, or $R^7$ and $R^8$ taken together with carbon atom to which is attached represents C3~7 cycloalkylene,

is carbocyclic ring or hetero ring,

===== is double bond or triple bond,
m and n each independently, is 1~3.) a non-toxic salt thereof, or a hydrate thereof,
(2) a peroxisome proliferator activated receptor regulator containing a compound of formula (I), a non-toxic salt thereof, or a hydrate thereof as active ingredient, and (3) a process for the preparation of a compound of formula (I).

DETAILED EXPLANATION

Unless otherwise specified, all isomers are included in the present invention. For example, alkyl, alkoxy and alkylthio group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, l-isomer), polar compounds generated by chromatographic separation (more polar compound, less polar compound), equilibrium compounds, mixtures thereof at voluntary ratios and racemic mixtures are also included in the present invention.

In the formula (I), C1~8 alkyl represented by $R^1$ and $R^2$ means methyl, ethyl, propyl, butyl, pentyl, hexyl, heptyl, octyl and isomers thereof.

In the formula (I), C1~4 alkyl represented by $R^3$, $R^4$, $R^5$, $R^6$, $R^7$ and $R^8$, or C1~4 alkyl as a substituent of carbocyclic ring or hetero ring represented by $R^1$, means methyl, ethyl, propyl, butyl and isomers thereof.

In the formula (I), C1~4 alkoxy represented by $R^1$ and $R^2$, or C1~4 alkoxy as a substituent of carbocyclic ring or hetero ring represented by $R^1$, means methoxy, ethoxy, propoxy, butoxy and isomers thereof.

In the formula (I), C1~4 alkylthio represented by $R^1$ and $R^2$ means methylthio, ethylthio, propylthio, butylthio and isomers thereof.

In the formula (I), halogen represented by $R^1$ and $R^2$, or halogen as a substituent of carbocyclic ring or hetero ring represented by $R^1$, means fluoride, chloride, bromide and iodide.

In the formula (I), C3~7 cycloalkylene represented by $R^7$ and $R^8$ taken together with carbon atom to which is attached means cyclopropylene, cyclobutylene, cyclopentylene, cyclohexylene and cycloheptylene.

In the formula (I), carbocyclic ring represented by $R^1$ and

means C3~10 mono-, or bi-cyclic carbocyclic ring and bridged carbocyclic ring. For example, C3~10 mono-, or bi-cyclic carbocyclic ring and bridged carbocyclic ring means cyclopropane, cyclobutane, cyclopentane, cyclohexane, cycloheptane, cyclooctane, cyclononane, cyclodecane, cyclopentene, cyclohexene, cyclopentadiene, cyclohexadiene, benzene, pentalene, indene, naphthalene, azulene, dihydronaphthalene, tetrahydronaphthalene, perhydronaphthalene, indane(dihydroindene), perhydroindene, bicyclopentane, bicyclohexane, bicycloheptane ([2.2.1]bicycloheptane), bicyclooctane, bicyclononane, bicyclodecane, adamantane etc.

In the formula (I), hetero ring represented by $R^1$ and

means unsaturated, or partially or completely saturated, 5~15 membered mono- or bi-cyclic hetero ring containing 1~3 of nitrogen atom(s), 1~2 of oxygen atom(s) and/or one sulfur atom. For example, unsaturated, or partially or completely saturated, 5~15 membered mono- or bi-cyclic hetero ring containing 1~3 of nitrogen atom(s), 1~2 of oxygen atom(s) and/or one sulfur atom, mean pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, dihydrofuran, tetrahydrofuran, dihydropyran, tetrahydropyran, dihydrothiophene, tetrahydrothiophene, dihydrothiine (dihydrothiopyran), tetrahydrothiine(tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrobenzoxazine, dioxaindan(1,3-dioxaindan), benzodioxane, quinuclidine, pyrrole, imidazole, pyrazole, pyridine, pyrazine, pyrimidine, pyridazine, azepine, diazepine, furan, pyran, oxepine, oxazepine, thiophene, thiin (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, oxatetrahydrofuran, imidazopyridine, benzotriazole etc.

In the compounds of formula (I), all groups represented by $X^1$ are preferable, and more preferable group is —N—.

In the compounds of formula (I), all groups represented by $X^2$ are preferable, and more preferable group is —O—.

In the compounds of formula (I), all groups represented by Y are preferable, and more preferable group is —O— or —S—, and most preferable groups is —O—.

In the compounds of formula (I), all groups represented by Z are preferable, and more preferable group is —S—, —SO—, or —SO$_2$—, and most preferable groups is —S—.

In the compounds of formula (I), 1~3 represented by n are all preferable, and more preferable is 1.

In the compounds of formula (I), all groups represented by

are preferable, and more preferable group is double bond. Furthermore, preferable group is double bond of trans form.

In the compounds of formula (I), all groups represented by are preferable, and more preferable group is unsaturated, or partially or completely saturated, 5~10 membered mono- or bi-cyclic hetero ring containing 1~2 of nitrogen atom(s), 1~2 of oxygen atom(s) and/or one sulfur atom. Furthermore, preferable groups are cyclopentane, cyclohexane, cycloheptane, benzene, furan, thiophene, pyridine, quinoline, dioxaindan (e.g. 1,3-dioxaindan).

In the present invention, PPAR regulator includes all the regulators of PPARα, γ, δ, α+γ, α+δ, γ+δ and α+γ+δ. Preferable regulatory fashion is, PPARα regulator, PPARγ regulator, PPARδ regulator, PPARα+γ regulator, PPARα+δ regulator, more preferably PPARα+γ regulator. PPAR regulator also includes PPAR agonist and PPAR antagonist, preferably PPAR agonist, more preferably PPARα agonist, PPARγ agonist, PPARδ agonist, PPARα+γ agonist or PPARα+δ agonist, particularly preferably PPARα+γ agonist.

Among the compounds of formula (I), preferable ones are, a compound of formula (Ia)

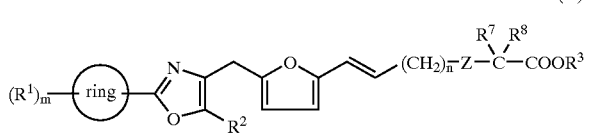
(Ia)

(wherein all symbols are the same meanings as hereinbefore described.), a compound of formula (Ib)

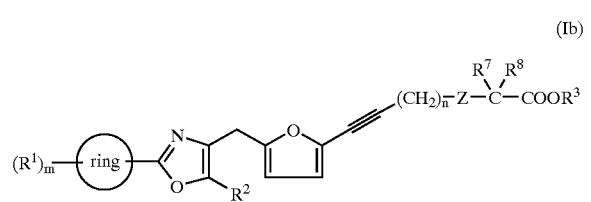
(Ib)

(wherein all symbols are the same meanings as hereinbefore described.), a compound of formula (Ic)

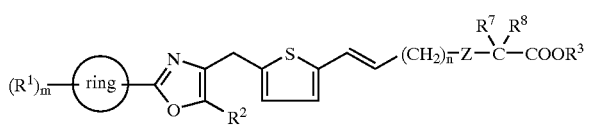
(Ic)

(wherein all symbols are the same meanings as hereinbefore described.), a compound of formula (Id)

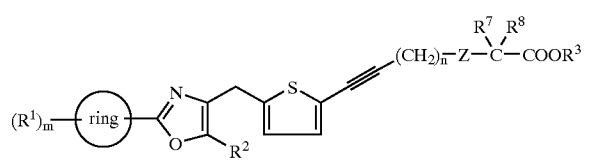
(Id)

(wherein all symbols are the same meanings as hereinbefore described.), a compound of formula (Ie)

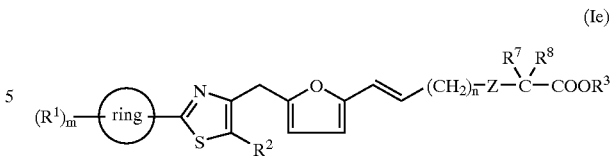
(Ie)

(wherein all symbols are the same meanings as hereinbefore described.), a compound of formula (If)

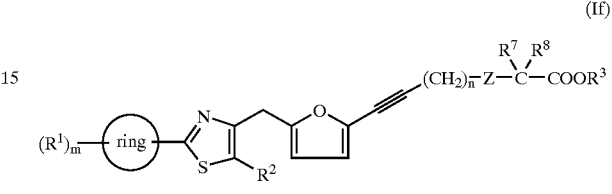
(If)

(wherein all symbols are the same meanings as hereinbefore described.), a compound of formula (Ig)

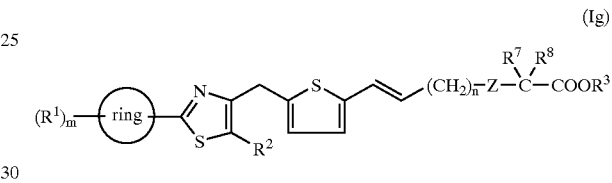
(Ig)

(wherein all symbols are the same meanings as hereinbefore described.), a compound of formula (Ih)

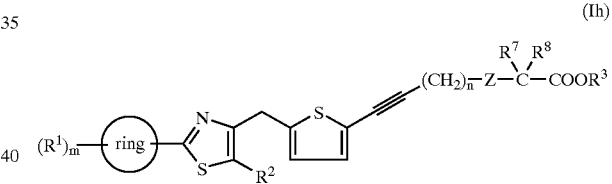
(Ih)

(wherein all symbols are the same meanings as hereinbefore described.), a non-toxic salts thereof, or a hydrate thereof.

Concrete compounds are the compounds shown in the following Tables 1~24, a non-toxic salts thereof and a hydrate thereof, and compounds described in Example hereinafter.

In the each Table, Me is methyl, Et is ethyl, n-Pr is normalpropyl, n-But is normalbutyl and the other symbols are the same meanings as hereinbefore described.

TABLE 1

(Ia-1)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |

TABLE 1-continued

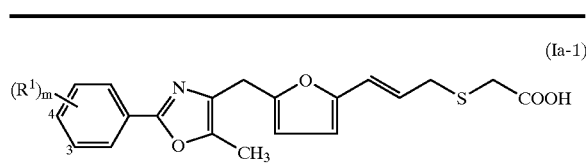
(Ia-1)

| No. | (R¹)ₘ | No. | (R¹)ₘ |
|---|---|---|---|
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 2

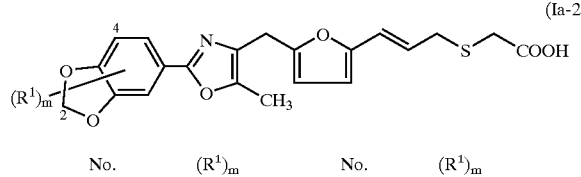
(Ia-2)

| No. | (R¹)ₘ | No. | (R¹)ₘ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-CF₃ | 21 | 2-Cl |
| 9 | 4-CF₃O | 22 | 2,2-di-F |
| 10 | 4-MeS | 23 | 2,2-di-Cl |
| 11 | 4-MeO | | |
| 12 | 4-NO₂ | | |
| 13 | 4-CN | | |

TABLE 3

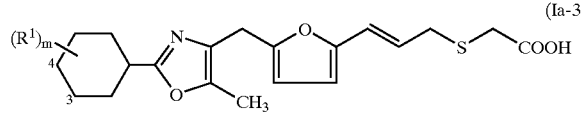
(Ia-3)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 4

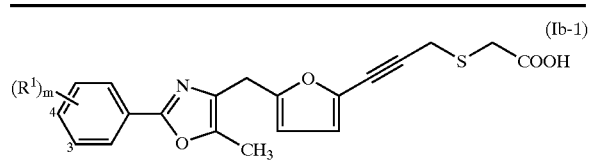
(Ib-1)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 5

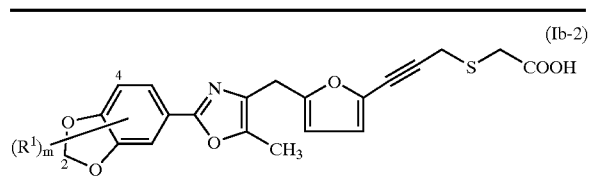
(Ib-2)

| No. | (R¹)ₘ | No. | (R¹)ₘ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-CF₃ | 21 | 2-Cl |
| 9 | 4-CF₃O | 22 | 2,2-di-F |
| 10 | 4-MeS | 23 | 2,2-di-Cl |
| 11 | 4-MeO | | |
| 12 | 4-NO₂ | | |
| 13 | 4-CN | | |

TABLE 6

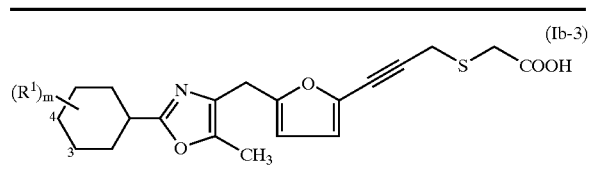
(Ib-3)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |

TABLE 6-continued (Ib-3)

| No. | (R¹)ₘ | No. | (R¹)ₘ |
|---|---|---|---|
| 12 | 4-NO₂ | 25 | 3-CN |
| 13 | 4-CN | 26 | 3,4-di-MeO |

TABLE 7

(Ic-1)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 8

(Ic-2)

| No. | (R¹)ₘ | No. | (R¹)ₘ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-CF₃ | 21 | 2-Cl |
| 9 | 4-CF₃O | 22 | 2,2-di-F |
| 10 | 4-MeS | 23 | 2,2-di-Cl |
| 11 | 4-MeO | | |
| 12 | 4-NO₂ | | |
| 13 | 4-CN | | |

TABLE 9

(Ic-3)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 10

(Id-1)

| No. | (R¹)ₘ | No. | (R¹)ₘ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF₃ |
| 8 | 4-CF₃ | 21 | 3-CF₃O |
| 9 | 4-CF₃O | 22 | 3-MeS |
| 10 | 4-MeS | 23 | 3-MeO |
| 11 | 4-MeO | 24 | 3-NO₂ |
| 12 | 4-NO₂ | 25 | 3-CN |
| 13 | 4-CN | 26 | 3,4-di-MeO |

TABLE 11

(Id-2)

| No. | (R¹)ₘ | No. | (R¹)ₘ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-CF₃ | 21 | 2-Cl |
| 9 | 4-CF₃O | 22 | 2,2-di-F |
| 10 | 4-MeS | 23 | 2,2-di-Cl |

TABLE 11-continued (Id-2)

| No. | $(R^1)_m$ | No. | $(R^1)_m$ |
|---|---|---|---|
| 11 | 4-MeO | | |
| 12 | 4-NO$_2$ | | |
| 13 | 4-CN | | |

TABLE 12

(Id-3)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF$_3$ |
| 8 | 4-CF$_3$ | 21 | 3-CF$_3$O |
| 9 | 4-CF$_3$O | 22 | 3-MeS |
| 10 | 4-MeS | 23 | 3-MeO |
| 11 | 4-MeO | 24 | 3-NO$_2$ |
| 12 | 4-NO$_2$ | 25 | 3-CN |
| 13 | 4-CN | 26 | 3,4-di-MeO |

TABLE 13

(Ie-1)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF$_3$ |
| 8 | 4-CF$_3$ | 21 | 3-CF$_3$O |
| 9 | 4-CF$_3$O | 22 | 3-MeS |
| 10 | 4-MeS | 23 | 3-MeO |
| 11 | 4-MeO | 24 | 3-NO$_2$ |
| 12 | 4-NO$_2$ | 25 | 3-CN |
| 13 | 4-CN | 26 | 3,4-di-MeO |

TABLE 14

(Ie-2)

| No. | $(R^1)_m$ | No. | $(R^1)_m$ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-CF$_3$ | 21 | 2-Cl |
| 9 | 4-CF$_3$O | 22 | 2,2-di-F |
| 10 | 4-MeS | 23 | 2,2-di-Cl |
| 11 | 4-MeO | | |
| 12 | 4-NO$_2$ | | |
| 13 | 4-CN | | |

TABLE 15

(Ie-3)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF$_3$ |
| 8 | 4-CF$_3$ | 21 | 3-CF$_3$O |
| 9 | 4-CF$_3$O | 22 | 3-MeS |
| 10 | 4-MeS | 23 | 3-MeO |
| 11 | 4-MeO | 24 | 3-NO$_2$ |
| 12 | 4-NO$_2$ | 25 | 3-CN |
| 13 | 4-CN | 26 | 3,4-di-MeO |

TABLE 16

(If-1)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-CF$_3$ |
| 8 | 4-CF$_3$ | 21 | 3-CF$_3$O |
| 9 | 4-CF$_3$O | 22 | 3-MeS |
| 10 | 4-MeS | 23 | 3-MeO |
| 11 | 4-MeO | 24 | 3-NO$_2$ |
| 12 | 4-NO$_2$ | 25 | 3-CN |
| 13 | 4-CN | 26 | 3,4-di-MeO |

TABLE 17

(If-2)

| No. | $(R^1)_m$ | No. | $(R^1)_m$ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-$CF_3$ | 21 | 2-Cl |
| 9 | 4-$CF_3O$ | 22 | 2,2-di-F |
| 10 | 4-MeS | 23 | 2,2-di-Cl |
| 11 | 4-MeO | | |
| 12 | 4-$NO_2$ | | |
| 13 | 4-CN | | |

TABLE 18

(If-3)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-$CF_3$ |
| 8 | 4-$CF_3$ | 21 | 3-$CF_3O$ |
| 9 | 4-$CF_3O$ | 22 | 3-MeS |
| 10 | 4-MeS | 23 | 3-MeO |
| 11 | 4-MeO | 24 | 3-$NO_2$ |
| 12 | 4-$NO_2$ | 25 | 3-CN |
| 13 | 4-CN | 26 | 3,4-di-MeO |

TABLE 19

(Ig-1)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-$CF_3$ |
| 8 | 4-$CF_3$ | 21 | 3-$CF_3O$ |
| 9 | 4-$CF_3O$ | 22 | 3-MeS |
| 10 | 4-MeS | 23 | 3-MeO |
| 11 | 4-MeO | 24 | 3-$NO_2$ |

TABLE 19-continued (Ig-1)

| No. | $(R^1)_m$ | No. | $(R^1)_m$ |
|---|---|---|---|
| 12 | 4-$NO_2$ | 25 | 3-CN |
| 13 | 4-CN | 26 | 3,4-di-MeO |

TABLE 20

(Ig-2)

| No. | $(R^1)_m$ | No. | $(R^1)_m$ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-$CF_3$ | 21 | 2-Cl |
| 9 | 4-$CF_3O$ | 22 | 2,2-di-F |
| 10 | 4-MeS | 23 | 2,2-di-Cl |
| 11 | 4-MeO | | |
| 12 | 4-$NO_2$ | | |
| 13 | 4-CN | | |

TABLE 21

(Ig-3)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-$CF_3$ |
| 8 | 4-$CF_3$ | 21 | 3-$CF_3O$ |
| 9 | 4-$CF_3O$ | 22 | 3-MeS |
| 10 | 4-MeS | 23 | 3-MeO |
| 11 | 4-MeO | 24 | 3-$NO_2$ |
| 12 | 4-$NO_2$ | 25 | 3-CN |
| 13 | 4-CN | 26 | 3,4-di-MeO |

TABLE 22

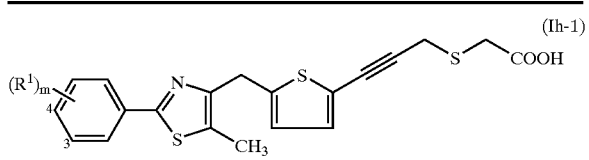
(Ih-1)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-$CF_3$ |
| 8 | 4-$CF_3$ | 21 | 3-$CF_3O$ |
| 9 | 4-$CF_3O$ | 22 | 3-MeS |
| 10 | 4-MeS | 23 | 3-MeO |
| 11 | 4-MeO | 24 | 3-$NO_2$ |
| 12 | 4-$NO_2$ | 25 | 3-CN |
| 13 | 4-CN | 26 | 3,4-di-MeO |

TABLE 23

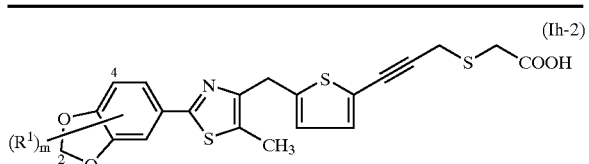
(Ih-2)

| No. | $(R^1)_m$ | No. | $(R^1)_m$ |
|---|---|---|---|
| 1 | H | 14 | 2-Me |
| 2 | 4-Me | 15 | 2-Et |
| 3 | 4-Et | 16 | 2-n-Pr |
| 4 | 4-n-Pr | 17 | 2-n-but |
| 5 | 4-n-but | 18 | 2,2-di-Me |
| 6 | 4-F | 19 | 2,2-di-Et |
| 7 | 4-Cl | 20 | 2-F |
| 8 | 4-$CF_3$ | 21 | 2-Cl |
| 9 | 4-$CF_3O$ | 22 | 2,2-di-F |
| 10 | 4-MeS | 23 | 2,2-di-Cl |
| 11 | 4-MeO | | |
| 12 | 4-$NO_2$ | | |
| 13 | 4-CN | | |

TABLE 24

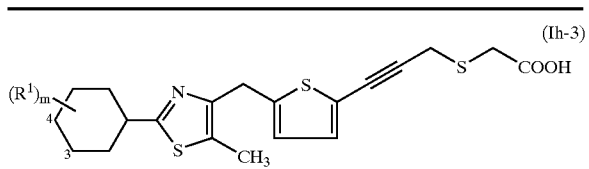
(Ih-3)

| No. | $(R^1)_m$ | No. | $(R^1)_m$ |
|---|---|---|---|
| 1 | H | 14 | 3-Me |
| 2 | 4-Me | 15 | 3-Et |
| 3 | 4-Et | 16 | 3-n-Pr |
| 4 | 4-n-Pr | 17 | 3-n-but |
| 5 | 4-n-but | 18 | 3-F |
| 6 | 4-F | 19 | 3-Cl |
| 7 | 4-Cl | 20 | 3-$CF_3$ |
| 8 | 4-$CF_3$ | 21 | 3-$CF_3O$ |
| 9 | 4-$CF_3O$ | 22 | 3-MeS |
| 10 | 4-MeS | 23 | 3-MeO |
| 11 | 4-MeO | 24 | 3-$NO_2$ |

TABLE 24-continued

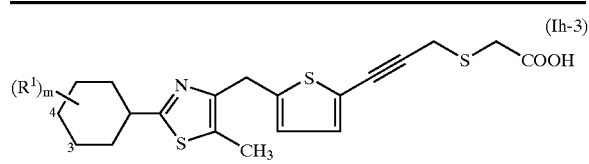
(Ih-3)

| No. | $(R^1)_m$ | No. | $(R^1)_m$ |
|---|---|---|---|
| 12 | 4-$NO_2$ | 25 | 3-CN |
| 13 | 4-CN | 26 | 3,4-di-MeO |

[Process for the Preparation of the Compound of the Present Invention]

(a) In the compound of formula (I), the compound wherein Z is —O—, —S—, and $R^3$ is C1~4 alkyl, i.e., the compound of formula (I-A)

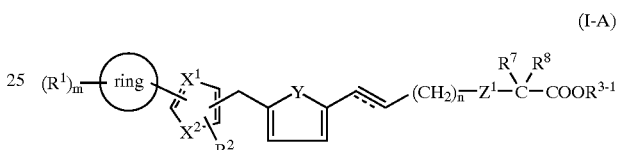
(I-A)

(wherein $Z^1$ is —O—, —S—, $R^{3-1}$ is C1~4 alkyl, the other symbols are the same meanings as hereinbefore described.) may be prepared by reacting the compound of formula (II)

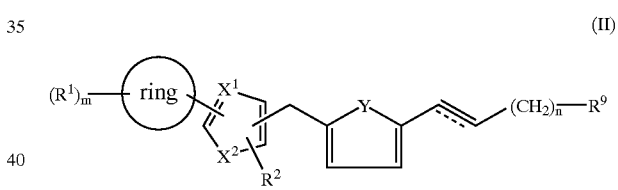
(II)

(wherein $R^9$ is methanesulfonyloxy or halogen, the other symbols are the same meanings as hereinbefore described.) with the compound of formula (III)

(III)

(wherein $Z^{1-1}$ is —OH or —SH, the other symbols are the same meanings as hereinbefore described.).

This reaction is known, for example, may be carried out in an organic solvent (tetrahydrofuran (THF), diethylether, dichloromethane, chloroform, carbon tetrachloride, pentane, hexane, benzene, toluene, dimethylformamide (DMF), dimethylsulfoxide (DMSO), hexamethylphosphoramide (HMPA) etc.), in the presence of base (sodium hydroxide, potassium carbonate, triethylamine, pyridine, sodium iodide, cesium carbonate etc.) at 0~80° C.

(b) In the compound of formula (I), the compound wherein Z is —O—, —S—, and $R^3$ is hydrogen, i.e., the compound of formula (I-B)

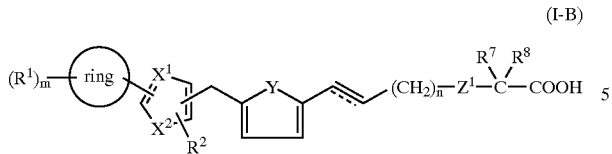

(I-B)

(wherein all symbols are the same meaning as hereinbefore described.) may be prepared by hydrolysis reaction of the compound of formula (I-A).

The said hydrolysis reaction is known, for example, may be carried out (1) in an organic solvent admissible with water (THF, dioxane, ethanol, methanol etc.) or mixture solvent thereof, using an aqueous solution of alkali (potassium hydroxide, sodium hydroxide, potassium carbonate, sodium carbonate etc.), or
(2) in alkanol (methanol, ethanol etc.), using the above alkali under an anhydrous condition. These reactions may be carried out at 0~100° C. normally.

(c) In the compound of formula (I), p is 1 or 2, namely, Z is —SO— or —SO$_2$—, i.e., the compound of formula (I-C)

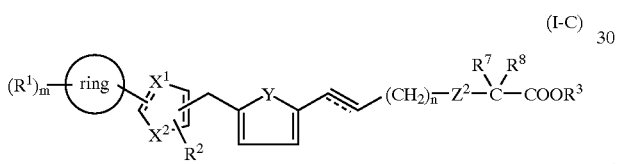

(I-C)

(wherein $Z^2$ is —SO— or —SO$_2$—, the other symbols are the same meanings as hereinbefore described.) may be prepared by oxidation of the compound of formula (I-A) or formula (I-B) wherein $Z^1$ is —S—.

The compound of formula (I-C) wherein $Z^2$ is —SO$_2$—, may be also prepared by oxidation of the compound of formula (I-C) wherein $Z^2$ is —SO—.

This oxidation is known, for example, may be carried out in an organic solvent (THF, dichloromethane, chloroform etc.), using a necessary amount of oxidizing agent (perhydrogen oxide, sodium periodate, acyl nitrite, sodium perboronate, peracid (e.g., 3-chloroperbenzoic acid, peracetic acid, OXONE (trade mark)) etc.) at 0~50° C.

The compounds of formulae (II) and (III) are known per se or may be prepared by known methods.

For example, in the compound of formula (III), 2-mercaptoacetic acid.methyl ester(thioglycolic acid methyl) has been marketed.

For example, the compound of formula (II) may be prepared according to the following Schemes 1~2.

In each Scheme, the abbreviation and symbols are as the following meanings, and the other symbols are the same meanings as hereinbefore described.

Me: methyl,
Bu: n-butyl,
$R^{10}$: halogen,
Pd(PPh$_3$)$_4$: tetrakis(triphenylphosphine)palladium,
n': 0~2,
$R^{11}$: C1~4 alkyl.

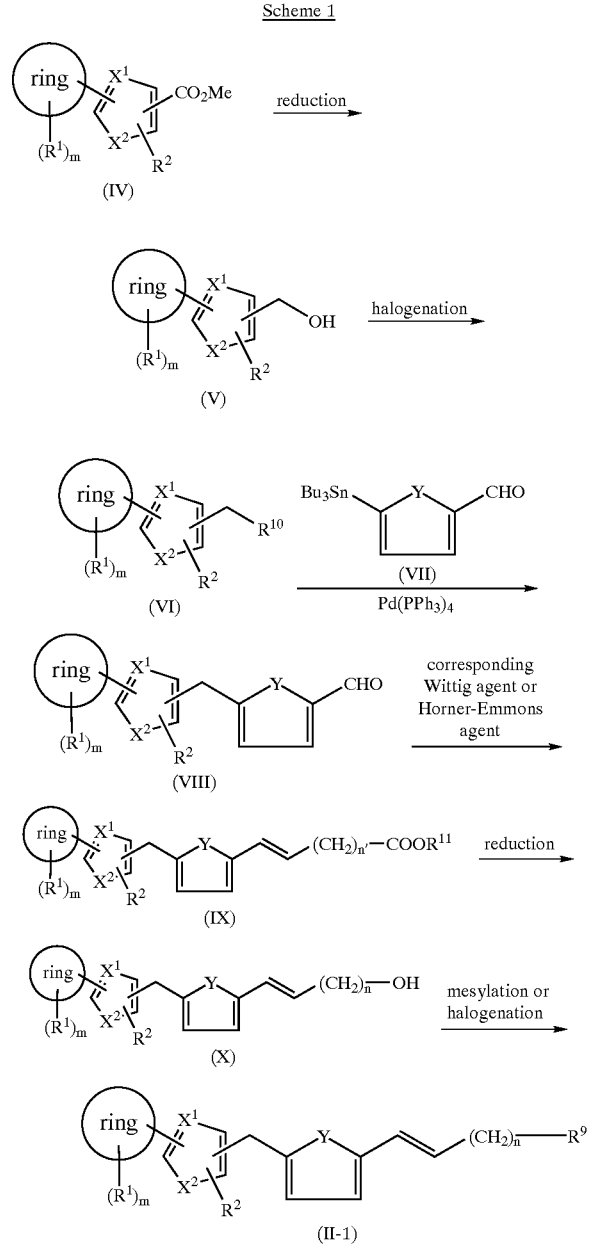

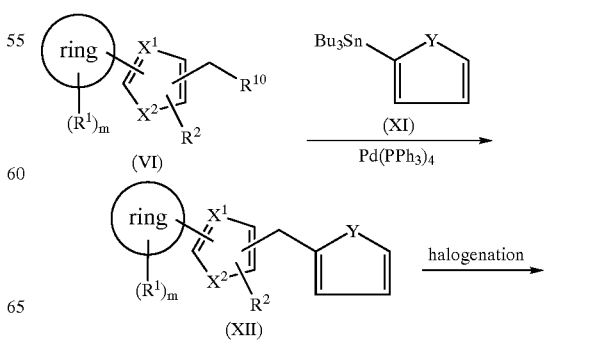

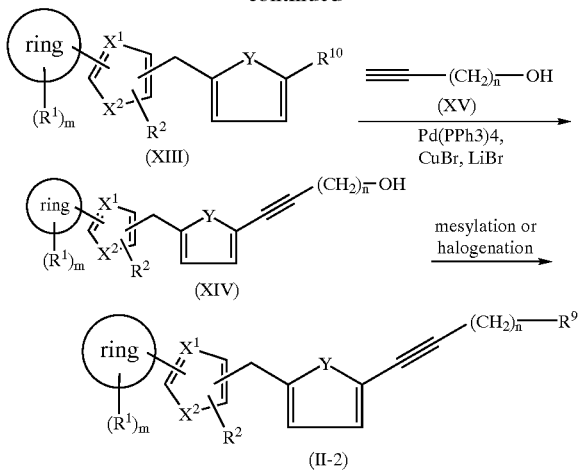

The compounds of formulae (IV), (VII), (XI) and (XV) are known per se or may be prepared by known methods.

The reactions described in the above-mentioned Schemes may be carried out by known methods.

In the present invention, the other starting materials and each reagent are known per se or may be prepared by known methods.

In each reaction in the present specification, products may be purified by a conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction or after a series of reactions.

All the non-toxic salts are also included in the present invention. For example, the compounds of the formula (I) of the present invention may be converted into the corresponding salts by known methods. Non-toxic and water-soluble salts are preferable. Suitable salts, for example, are follows:

salts of alkaline metals (potassium, sodium etc.), salts of alkaline earth metals (calcium, magnesium etc.), ammonium salts, salts of pharmaceutically acceptable organic amines (tetramethylammonium, triethylamine, methylamine, dimethylamine, cyclopentylamine, cyclohexylamine, benzylamine, phenethylamine, piperidine, monoethanolamine, diethanolamine, tris (hydroxymethyl)amine, lysine, arginine, N-methyl-D-glucamine etc.).

The compounds of formula (I) of the present invention may be converted into the corresponding acid additional salts by methods known per se. Non-toxic and water-soluble acid addition salts are preferable. Suitable acid addition salts, for example, are salts of inorganic acids, e.g., hydrochloride, hydrobromide, sulphate, phosphate, nitrate etc., or salts of organic acids, e.g., acetate, trifluoroacetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of formula (I) of the present invention or salts thereof may be converted into hydrate thereof by methods known per se.

[Pharmacological Activity]

It was confirmed that a compound of the present invention of formula (I) has PPAR regulating activities by the following experiments.

Measurement of PPARα Agonistic and PPARγ Agonistic Activities (1) Preparation of Materials in Luciferase Assay Using Human PPAR α or δ

The whole operations were carried out by the basic methods in gene engineering techniques and the conventional methods in yeast One-hybrid or Two-hybrid system.

As a luciferase gene expression vector under the control of thymidine kinase (TK) promotor, luciferase structural gene was excised from PicaGene Basic Vector 2 (trade name, Toyo Ink Inc., catalogue No. 309-04821), to prepare luciferase gene expression vector pTK-Luc. under the control of TK promotor (−105/+51) as a minimum essential promotor activity from pTKβ having TK promotor (Chrontech Inc., catalogue No. 6179-1). In the upper stream of TK promotor, four times repeated UAS sequence was inserted, which is the response element of Gal4 protein, a basic transcription factor in yeast, to construct 4×UAS-TK-Luc. as reporter gene. The following is the enhancer sequence used (Sequence No. 1).

Sequence No. 1

Enhancer sequence repeating Gal4 response element four-times tande mly.

5'-T(CGACGGAGTACTGTCCTCCG)×4 AGCT-3'

A vector was prepared as described hereafter which expresses chimeric receptor protein wherein in carboxy terminus of yeast Gal4 protein DNA binding domain was fused to ligand binding domain of human PPAR α or γ. That is to say, PicaGene Basic Vector 2 (trade name, Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Gal4 DNA binding domain, the 1st to 147th amino acid sequence linked to the ligand binding domain of human PPARα or γ in frame was inserted to the downstream of promotor/enhancer in PicaGene Basic Vector 2 (trade name, Toyo Ink Inc., catalogue No. 309-04821). Here the DNA was aligned as follows; in the amino terminus of human PPARα or γ ligand binding domain, nuclear translocation signal originated from SV-40 T-antigen, Ala Pro Lys Lys Lys Arg Lys Val Gly (sequence No. 2) was added to make fusion protein localizing intranuclearly. On the other hand, in the carboxy terminus of them, influenza hemagglutinin epitope, Tyr Pro Tyr Asp Val Pro Asp Tyr Ala (sequence No. 3) and stop codon for translation was added in this order, to detect an expressed fused protein tagged epitope sequence.

According to the comparison of human PPAR structures described in the literatures by R. Mukherjee at al. (See J. Steroid Biochem. Molec. Biol., 51, 157 (1994)), M. E. Green et al., (See Gene Expression., 4, 281 (1995)), A. Elbrecht et al. (See Biochem Biophys. Res. Commun., 224, 431 (1996)) or A. Schmidt et al. (See Mol. Endocrinology., 6, 1634 (1992)), the portion of structural gene used as ligand binding domain of human PPARα or γ was DNA encoding the following peptide:

human PPARα ligand binding domain: $Ser^{167}$-$Tyr^{468}$ human PPARγ ligand binding domain: $Ser^{176}$-$Tyr^{478}$ (each human PPARγ1 ligand binding domain and human PPARγ2 ligand binding domain is $Ser^{204}$-$Tyr^{506}$ which is identical sequence each other).

In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase Assay Using Human PPARα or γ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2 \times 10^6$ cells were seeded in a 10 cm dish, and once washed with the medium without serum, followed by addition of the medium (10 ml) thereto. Reporter genie (10 μg), Gal4-PPAR expression vector (0.5 μg) and 50 μl of LipofectAMINE (GIBRO BRL Inc., catalogue No. 18324-012) were well mixed and added to the culture to introduce these DNAs into the host cells. They were cultured at 37° C. for 5~6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/100 ml of DMEM-10% dialyzed serum/well. Several hours after the cultivation, when cells were attached to the plastic ware, then 100 μl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturer's instruction.

As to PPARα agonistic activity, the relative activity of the compounds of the present invention (10 μM) was shown in Table 25, under the condition that luciferase activity was defined as 1.0 in case of carbacyclin (10 μM) as a positive control compound, which could activate transcription of luciferase gene significantly to PPAR α (See Eur. J. Biochem., 233, 242 (1996); Genes & Development., 10, 974 (1996)).

As to PPARγ agonistic activity, the relative activity of the compounds of the present. invention (10 μM) was shown in Table 26, under the condition that luciferase activity was defined as 1.0 in case of troglitazone (10 μM) as a positive control compound, which could activate transcription of luciferase gene significantly to PPARγ (See Cell., 83, 863 (1995); Endocrinology., 137, 4189 (1996) and J. Med. Chem., 39, 665 (1996)) and has been already launched as hypoglycemic agent.

Furthermore, assay of each compound was carried out three times to examine its reproducibility and to confirm the dose dependent activity.

TABLE 25

| Example Nos. | Relative Activity to a positive control compound (carbacyclin = 1) |
|---|---|
| Example 3 | 2.6 |
| Example 3(1) | 1.5 |
| Example 3(2) | 3.1 |
| Example 3(3) | 1.8 |

TABLE 26

| Example Nos. | Relative Activity to a positive control compound (troglitazone = 1) |
|---|---|
| Example 3 | 2.3 |
| Example 3(1) | 1.1 |
| Example 3(2) | 2.3 |
| Example 3(3) | 2.2 |

Hypoglycemic and Hypolipidemic Effects

Male, 7-weeks old KKAy/Ta mice weighed from 35 to 40 g (five mice per group) were pre-breaded for approximately one week and acclimatized for three days on milled diet. On the first day of the experiment (Day 0), mice were divided into some groups according to weight, plasma glucose and triglyceride (TG) levels to minimize the differences among groups. From the next day for two days they were given compounds by food mixture containing 0.03% (w/w) of the compound of the present invention or by milled diet only. At 13:00 of the third day, blood samples were collected to measure glucose and TG levels. The results are shown in Table 27. Additionally, there was no significant difference in the food intake between control group (milled diet only) and compounds-treated group (milled diet containing 0.03% compounds).

TABLE 27

| Example Nos. | blood sugar level (mg/dl) 4 days | TG level (mg/dl) 4 days |
|---|---|---|
| Control | 520 ± 147 | 439 ± 234 |
| Example 3 46 mg/kg/day by food mixture (conversion value) | 260 ± 37* | 43 ± 12* |
| Example 3(1) 43 mg/kg/day by food mixture (conversion value) | 253 ± 27* | 44 ± 11* |
| Example 3(2) 44 mg/kg/day by food mixture (conversion value) | 243 ± 37* | 45 ± 12* |
| Example 3(3) 47 mg/kg/day by food mixture (conversion value) | 234 ± 31* | 31 ± 15* |

*:p < 0.01 vs control (5 mice per group)

Hypocholesterolemic and Hypolipidemic Effects

Male, six-weeks old SD rats (five rats per group) were left to take milled diet and water ad libitum and were acclimatized for 1 week.

At 9:00 on the first day of the experiment (Day 0), blood sampling was done from tail vein. The rats were divided into some groups according to body weight, triglyceride (TG), non-esterified fatty acid (NEFA) and total cholesterol (TC) levels to minimize differences of the parameters among the groups. At 17:00 of the day, the compound of the present invention dissolved in 0.5% aqueous solution of carboxymethylcellulose (CMC) was orally administered, and thereafter, with hypercholesterolemic food (5.5% peanut oil, 1.5% cholesterol and 0.5% cholic acid were mixed with milled CRF-1 diet, Charles River Inc.) was given to the rats.

At 9:00 of the next day, blood sampling was done from tail vein. The lipid levels in blood (TG, NEFA and TC levels) after administration of the compounds of the present invention were measured. The results are shown in Table 28.

There was no significant difference of the food intake between the control group (provided only 0.5% CMC) and the group treated with the compounds of the present invention.

TABLE 28

| Example Nos. | TC level (mg/dl) | TG level (mg/dl) | NEFA level (mEq/l) |
| --- | --- | --- | --- |
| Control | 167 ± 13 | 163 ± 18 | 615 ± 80 |
| Example 3 | 87 ± 5* | 73 ± 7* | 207 ± 25* |
| Example 3(1) | 107 ± 4* | 92 ± 26 | 394 ± 49* |
| Example 3(2) | 86 ± 6* | 62 ± 7* | 145 ± 18* |
| Example 3(3) | 91 ± 4* | 79 ± 12* | 213 ± 31* |

*: $p < 0.01$ vs control (5 rats per group)

The hypoglycemic or hypolipidemic effects observed in KKAy mice imply the possibility of preventives and/or remedies for diabetes and hyperlipidemia etc. Cholesterol-lowering and free fatty acid-lowering effects observed in high cholesterol diet-fed rats imply that the compounds of the present invention are useful as preventives and/or remedies of atherosclerosis etc.

The compounds of the present invention possess the hypoglycemic or hypolipidemic (TG, NEFA) effects as well as cholesterol-lowering effect, so they are expected to be more useful to compare with the marketed hypoglycemic or hypolipidemic drugs.

In addition, it has been known that hyperlipidemia, obesity or diabetes are one of cause of uncondition in liver function and hyperlipid in liver. Therefore, the compounds of the present invention are expected to be the drugs to improve liver function which has not been marketed.

INDUSTRIAL APPLICABILITY

[Effect]

The compound of formula (I) of the present invention, non-toxic salts thereof, acid addition salts thereof and hydrates thereof have PPAR regulating effect, and therefore are expected to be applied as hypoglycemic agents, hypolipidemic agents, preventives and/or remedies for diseases associated with metabolic disorders (diabetes, obesity, syndrome X, hypercholesterolemia and hyperlipoproteinemia etc.), hyperlipidemia, atherosclerosis, hypertension, circulatory diseases, overeating, coronary heart diseases etc., HDL cholesterol-elevating agents, LDL cholesterol and/or VLDL cholesterol-lowering agents and agents for relieving risk factors of diabetes or syndrome X.

The compound of formula (I) of the present invention, non-toxic salts thereof, acid addition salts thereof and hydrates thereof have particularly PPARα agonist and/or PPARγ agonist effect, and therefore are thought to be useful as hypoglycemic agents, hypolipidemic agents, preventives and/or remedies for diseases associated with metabolic disorders (diabetes, obesity, syndrome X, hypercholesterolemia, hyperlipoproteinemia etc.), hyperlipidemia, atherosclerosis, hypertension, circulatory diseases and overeating etc. Since they are expected to have HDL cholesterol-elevating effect, LDL cholesterol and/or VLDL cholesterol-lowering effect, inhibition of progress of atherosclerosis and its treatment, and inhibitory effect against obesity, they are also expected to be useful for the treatment and/or prevention of diabetes as hypoglycemic agents, for the amelioration of hypertension, for the relief from risk factors of syndrome X, and as preventives against occurrence of coronary heart diseases.

[Toxicity]

The toxicity of the compound of the present invention is very low and therefore, it may be considered that the compounds of the present invention are safe for pharmaceutical use.

[Application for Pharmaceuticals]

For the purpose above described, the compounds of the present invention of the formula (I), non-toxic salts and acid addition salts thereof and hydrates thereof may be normally administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, microcrystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution, plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOL-BATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or U.S. Pat. No. 3,095,355 may be used.

BEST MODE FOR CARRYING OUT THE INVENTION

The following Reference Examples and Examples illustrate the present invention, but do not limit the present invention.

The solvents in the parentheses show the developing or eluting solvents and the ratios of the solvents used are by volume in chromatographic separations and TLC.

Solvents in the parentheses of NMR show the solvents use for measurement.

Reference Example 1

5-methyl-2-phenyloxazol-4-ylcarboxylic acid.methyl ester

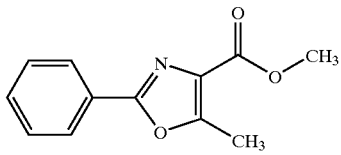

Benzaldehyde (11 ml) and hydroxyiminoacetoacetic acid-.methyl ester (18.8 g) were dissolved into acetic acid (35 ml) and the resultant solution was saturated by hydrochloric acid under cooling with ice, and was stirred for 2 hours. The reaction mixture was diluted with ether, and the precipitate was filtered out. The precipitate was suspended in acetic acid (200 ml), and a zinc powder (20 g) was added thereto under cooling with ice. The reaction mixture was stirred for 30 minutes on water bath. The reaction mixture was filtered off in order to exclude a zinc powder. A purified water was add to the filtrate, and the precipitate was filtered out. The precipitate was washed with a purified water, and dried over to give the title compound (11.7 g) having the following physical data.

TLC: Rf 0.44 (hexane:ethyl acetate=4:1);

NMR (CDCl$_3$): δ 8.14–8.02 (m, 2H), 7.51–7.42 (m, 3H), 3.95 (s, 3H), 2.72 (s, 3H).

Reference Example 2

(5-methyl-2-phenyloxazol-4-yl)methanol

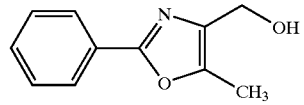

Lithium aluminum hydride (3.07 g) was suspended in anhydrous tetrahydrofuran (40 ml), and a solution of the compound prepared in Reference Example 1 (11.7 g) in anhydrous tetrahydrofuran (40 ml) was added dropwise thereto under cooling with ice. The reaction mixture was stirred for 15 minutes. A saturated aqueous solution of sodium sulfate (10 ml) was added dropwise to the reaction mixture slowly, and the reaction mixture was filtered off. The filtrate was concentrated to give the title compound (7.92 g) having the following physical data.

TLC: Rf 0.19 (hexane:ethyl acetate=2:1);

NMR (CDCl$_3$): δ 8.04–7.93 (m, 2H), 7.48–7.38 (m, 3H), 4.60 (s, 2H), 2.40 (s, 3H).

Reference Example 3

5-methyl-2-phenyloxazol-4-ylmethyl bromide

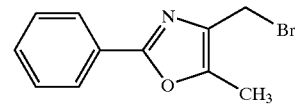

Triphenylphosphine (8.32 g) and carbon tetrabromide (10.5 g) were added to a solution of the compound prepared in Reference Example 2 (4.0 g) in dichloromethane (210 ml), and the resultant solution was stirred for 4 hours at room temperature. The reaction mixture was concentrated. The residue was purified by silica gel column chromatography (hexane:ethyl acetate=8:1) to give the title compound (4.93 g) having the following physical data.

TLC: Rf 0.66 (hexane:ethyl acetate=4:1);

NMR (CDCl$_3$): δ 8.06–7.94 (m, 2H), 7.48–7.38 (m, 3H), 4.45 (s, 2H), 2.41 (s, 3H).

Reference Example 4

2-formyl-5-(5-methyl-2-phenyloxazol-4-ylmethyl) furan

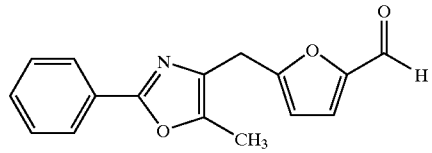

Under an atmosphere of argon gas, tetrakis (triphenylphosphine)palladium (1.13 g) was add to a solution of the compound prepared in Reference Example 3 (4.93 g) and 5-n-butylstannyl-2-furaldehyde (9.0 g) in dimethylformamide (100 ml), and the resultant solution was stirred for 1 hour at 70° C. Ice water was added to the reaction mixture, and it was extracted with ethyl acetate. The extract was washed with a 10% aqueous solution of ammonia and a saturated aqueous solution of sodium chloride, successively, dried over anhydrous magnesium sulfate and concentrated. The residue was purified by silica gel column chromatography (hexane:ethyl acetate=4:1) to give the title compound (3.38 g) having the following physical data.

TLC: Rf 0.39 (hexane:ethyl acetate=2:1);

NMR (CDCl$_3$): δ 9.55 (s, 1H), 8.04–7.92 (m, 2H), 7.48–7.38 (m, 3H), 7.18 (d, J=3.6 Hz, 1H), 6.35 (d, J=3.6 Hz, 1H), 3.99 (s, 2H), 2.36 (s, 3H).

Reference Example 5

(2E)-3-(5-(5-methyl-2-phenyloxazol-4-ylmethyl)furan-2-yl)-2-propenoic acid.ethyl ester

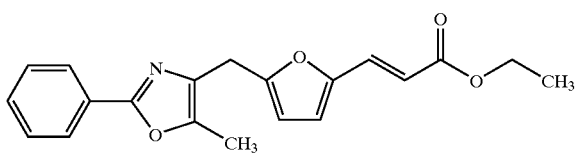

Under cooling with ice, diethylphosphonoacetic acid.ethyl ester ((2.97 ml) was added dropwise to a suspension of sodium hydride (610 mg) in tetrahydrofuran (60 ml) under an atmosphere of argon gas, and the resultant solution was stirred for 1 hour at room temperature. Ice water was added to the reaction mixture, and it was extracted with ethyl acetate. The extract was washed with a purified water and a saturated aqueous solution of sodium chloride, successively, dried over anhydrous magnesium sulfate and concentrated. The residue was purified by silica gel column chromatography (hexane:ethyl acetate=4:1) to give the title compound (4.03 g) having the following physical data.

TLC: Rf 0.65 (hexane:ethyl acetate=2:1);

NMR (CDCl$_3$): δ8.04–7.93 (m, 2H), 7.48–7.32 (m, 4H), 6.53 (d, J=3.0 Hz, 1H), 6.29–6.16 (m, 2H), 4.23 (q, J=7.0 Hz, 2H), 3.92 (s, 2H), 2.34 (s, 3H), 1.31 (t, J=7.0 Hz, 3H).

Reference Example 6

(2E)-3-(5-(5-methyl-2-phenyloxazol-4-ylmethyl)furan-2-yl)-2-propenol

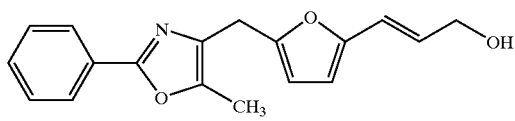

A solution of the compound prepared in Reference Example 5 (3.03 g) in anhydrous tetrahydrofuran (90 ml) was cooled to −78° C., and under an atmosphere of argon gas, diisobutylaluminum hydride (0.94 M hexane solution, 33 ml) was added thereto gradually. After confirmation of reaction completion, a saturated aqueous solution of sodium sulfate (5 ml) was added dropwise to the reaction mixture slowly, and it was warmed to room temperature. The deposited insoluble material was filtered out. The filtrate was concentrated to give the tittle compound (2.65 g) having the following physical data.

TLC: Rf 0.31 (hexane:ethyl acetate=2:1);

NMR (CDCl$_3$): δ 8.04–7.92 (m, 2H), 7.48–7.36 (m, 3H), 6.39 (d, J=16.0 Hz, 1H), 6.22 (dt, J=16.0, 5.0 Hz, 1H), 6.15 (d, J=3.0 Hz, 1H), 6.07 (d, J=3.0 Hz, 1H), 4.28 (t, J=5.0 Hz, 2H), 3.90 (s, 2H), 2.31 (s, 3H).

EXAMPLE 1

2-((2E)-3-(5-(5-methyl-2-phenyloxazol-4-ylmethyl)furan-2-yl)-2-propenylthio)acetic acid.methyl ester

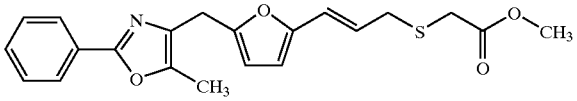

A solution of the compound prepared in Reference Example 6 (2.64 g) in dichloromethane (45 ml) was cooled to −50 ° C., and triethylamine (1.89 ml) and methanesulfonyl chloride (0.83 ml) were added thereto, and the resultant solution was stirred for 15 minutes. Diisopropylethylamine (7.8 ml) and thioglycolic acid.methyl ester (3.24 ml) were added to the reaction mixture, and it was stirred for 1 hour at −20° C. Ice water was added to the reaction mixture, and it was extracted with ethyl acetate. The extract was washed with a purified water and a saturated aqueous solution of sodium chloride, successively, dried over and concentrated. The residue was purified by silica gel column chromatography (hexane:ethyl acetate=9:1) to give the title compound (4.03 g) having the following physical data.

TLC: Rf 0.36 (hexane:ethyl acetate=4:1);

NMR (CDCl$_3$): δ 8.03–7.94 (m, 2H), 7.48–7.38 (m, 3H), 6.27 (d, J=15.6 Hz, 1H), 6.15 (d, J=3.0 Hz, 1H), 6.08 (d, J=3.0 Hz, 1H), 6.10–5.90 (m, 1H), 3.89 (s, 2H), 3.71 (s, 3H), 3.37 (d, J=7.0 Hz, 2H), 3.19 (s, 2H), 2.32 (s, 3H),

EXAMPLE 2~EXAMPLE 2(11)

The following compounds were obtained by the same procedure as a series of reactions of Reference Example 1→Reference Example 2→Reference Example 3→Reference Example 4→Reference Example 5→Reference Example 6→Example 1.

Also, The following compounds were used as starting compounds when the same procedure as Reference Example 1 was done.

EXAMPLE 2

4-methylbenzaldehyde

EXAMPLE 2(1), EXAMPLE 2(4) and EXAMPLE 2(5)

3,4-(methylenedioxy)benzaldehyde

EXAMPLE 2(2)

4-ethylbenzaldehyde

EXAMPLE 2(3)

benzaldehyde

EXAMPLE 2(6), 2(8), 2(9)

4-dimethylaminobenzaldehyde

EXAMPLE 2(7), 2(10), 2(11)

2-dimethylamino-5-pyridinecarbaldehyde

Also, in the case of Example 2(3), 5-n-butylstannyl-2-thienylaldehyde was used instead of 5-n-butylstannyl-2-furaldehyde in Reference Example 4.

Also, in the case of Example 2(4), Example 2(8) and Example 2(10), 2-mercapto-2-methylpropanoic acid.ethyl ester was used instead of thioglycolic acid -methyl ester in Example 1.

In the case of Example 2(5), Example 2(9) and Example 2(11), (1-mercapto)cyclobutanecarboxylic acid.ethyl ester was used instead of thioglycolic acid.methyl ester in Example 1.

EXAMPLE 2

2-((2E)-3-(5-(5-methyl-2-(4-methylphenyl)oxazol-4-ylmethyl)furan-2-yl)-2-propenylthio)acetic acid.methyl ester

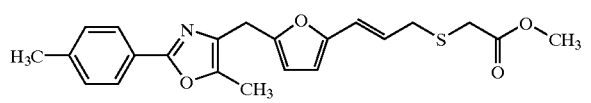

TLC: Rf 0.59 (hexane:ethyl acetate=2:1);

NMR (CDCl$_3$): δ 7.87 (d, J=8.0 Hz, 2H), 7.23 (d, J=8.0 Hz, 2H), 6.27 (d, J=15.8 Hz, 1H), 6.14 (d, J=3.2 Hz, 1H), 6.07 (d, J=3.2 Hz, 1H), 5.99 (dt, J=15.8, 7.6 Hz, 1H), 3.88 (s, 2H), 3.71 (s, 3H), 3.37 (d, J=7.6 Hz, 2H), 3.19 (s, 2H), 2.38 (s, 3H), 2.31 (s, 3H).

EXAMPLE 2(1)

2-((2E)-3-(5-(5-methyl-2-(1,3-dioxaindan-5-yl)oxazol-4-ylmethyl)furan-2-yl)-2-propenylthio)acetic acid.methyl ester

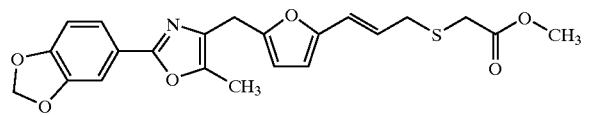

TLC: Rf 0.35 (hexane:ethyl acetate=4:1);

NMR (CDCl$_3$): δ 7.53 (dd, J=8.0, 1.5 Hz, 1H), 7.44 (d, J=1.5 Hz, 1H), 6.85 (d, J=8.0 Hz, 1H), 6.27 (d, J=16.0 Hz, 1H), 6.14 (d, J=3.0 Hz, 1H), 6.09–5.90 (m, 4H), 3.86 (s, 2H), 3.71 (s, 3H), 3.37 (d, J=7.5 Hz, 2H), 3.19 (s, 2H), 2.30 (s, 3H).

EXAMPLE 2(2)

2-((2E)-3-(5-(5-methyl-2-(4-ethylphenyl)oxazol-4-ylmethyl)furan-2-yl)-2-propenylthio)acetic acid.methyl ester

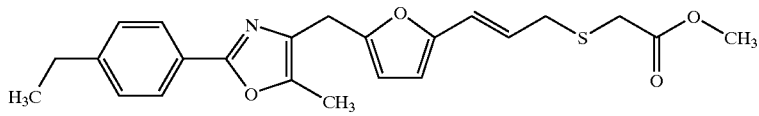

TLC: Rf 0.52 (hexane:ethyl acetate=3:1);

NMR (CDCl$_3$): δ 7.90 (d, J=8.3 Hz, 2H), 7.25 (d, J=8.3 Hz, 2H), 6.27 (d, J=15.8 Hz, 1H), 6.14 (d, J=3.2 Hz, 1H), 6.06 (d, J=3.2 Hz, 1H), 5.99 (dt, J=15.8, 7.8 Hz, 1H), 3.88 (s, 2H), 3.71 (s, 3H), 3.37 (d, J=7.8 Hz, 2H), 3.19 (s, 2H), 2.68 (q, J=7.6 Hz, 2H), 2.31 (s, 3H), 1.25 (t, J=7.6 Hz, 3H).

EXAMPLE 2(3)

2-((2E)-3-(5-(5-methyl-2-phenyloxazol-4-ylmethyl)thiophen-2-yl)-2-propenylthio)acetic acid.methyl ester

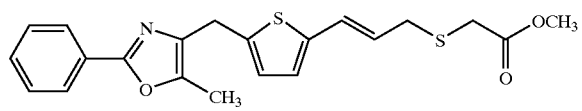

TLC: Rf 0.48 (ethyl acetate:hexane=1:3);

NMR (CDCl$_3$): δ 8.01–7.97 (m, 2H), 7.45–7.38 (m, 3H), 6.77–6.73 (m, 2H), 6.54 (br.d, J=15.4 Hz, 1H), 5.85 (dt, J=15.4, 7.6 Hz, 1H), 4.00 (s, 2H), 3.70 (s, 3H), 3.34 (br.d, J=7.6 Hz, 2H), 3.17 (s, 2H), 2.33 (s, 3H).

EXAMPLE 2(4)

2-methyl-2-((2E)-3-(5-(5-methyl-2-(1,3-dioxaindan-5-yl)oxazol-4-ylmethyl)furan-2-yl)-2-propenylthio)propanoic acid.ethyl ester

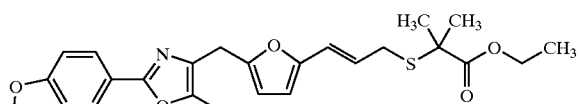

TLC: Rf 0.38 (ethyl acetate:hexane=1:3);

NMR (CDCl$_3$): δ 7.52 (dd, J=8.0, 2.0 Hz, 1H), 7.44 (d, J=2.0 Hz, 1H), 6.84 (d, J=8.0 Hz, 1H), 6.27 (d, J=15.5 Hz, 1H), 6.09 (d, J=3.0 Hz, 1H), 6.04 (d, J=3.0 Hz, 1H), 6.03 (dt, J=15.5, 7.5 Hz, 1H), 6.01 (s, 2H), 4.13 (q, J=7.0 Hz, 2H), 3.84 (s, 2H), 3.40 (d, J=7.5 Hz, 2H), 2.27 (s, 3H), 1.53 (s, 6H), 1.26 (t, J=7.0 Hz, 3H).

EXAMPLE 2(5)

1-((2E)-3-(5-(5-methyl-2-(1,3-dioxaindan-5-yl)oxazol-4-ylmethyl)furan-2-yl)-2-propenylthio)cyclobutanecarboxylic acid.ethyl ester

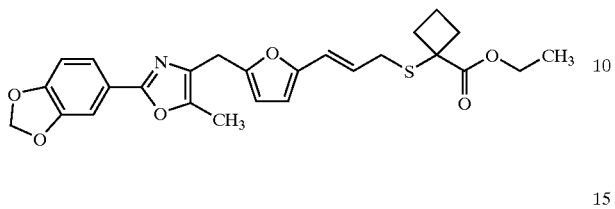

TLC: Rf 0.33 (ethyl acetate:hexane=1:3);

NMR (CDCl$_3$): δ 7.53 (dd, J=8.0, 2.0 Hz, 1H), 7.44 (d, J=2.0 Hz, 1H), 6.85 (d, J=8.0 Hz, 1H), 6.26 (d, J=15.5 Hz, 1H), 6.10 (d, J=1.5 Hz, 1H), 6.05 (dt, J=15.5, 7.0 Hz, 1H), 6.04 (d, J=1.5 Hz, 1H), 6.01 (s, 2H), 4.15 (q, J=7.0 Hz, 2H), 3.85 (s, 2H), 3.33 (d, J=7.0 Hz, 2H), 2.64 (m, 2H), 2.28 (s, 3H), 2.40–2.05 (m, 3H), 1.89 (m, 1 H), 1.26 (t, J=7.0 Hz, 3H).

EXAMPLE 2(6)

2-((2E)-3-(5-(5-methyl-2-(4-dimethylaminophenyl)oxazol-4-ylmethyl)furan-2-yl)-2-propenylthio)acetic acid.methyl ester

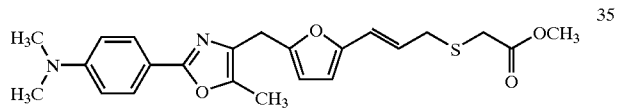

TLC: Rf 0.46 (hexane:ethyl acetate=2:1);

NMR (CDCl$_3$): δ 7.84 (m, 2H), 6.70 (m, 2H), 6.26 (d, J=15.6 Hz, 1H), 6.14 (d, J=3.2 Hz, 1H), 6.06 (d, J=3.2 Hz, 1H), 5.99 (dt, J=15.6, 7.2 Hz, 1H), 3.86 (s, 2H), 3.70 (s, 3H), 3.37 (d, J=7.2 Hz, 2H), 3.19 (s, 2H), 3.01 (s, 6H), 2.28 (s, 3H).

EXAMPLE 2(7)

2-((2E)-3-(5-(5-methyl-2-(2-dimethylaminopyridin-5-yl)oxazol-4-ylmethyl)furan-2-yl)-2-propenylthio)acetic acid.methyl ester

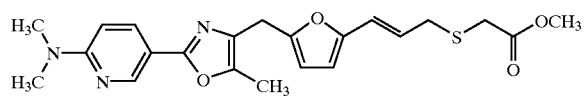

TLC: Rf 0.38 (hexane:ethyl acetate=1:1);

NMR (CDCl$_3$): δ 8.74 (dd, J=2.4, 0.8 Hz, 1H), 8.00 (dd, J=9.0, 2.4 Hz, 1H), 6.52 (dd, J=9.0, 0.8 Hz, 1H), 6.27 (d, J=15.6 Hz, 1H), 6.14 (d, J=3.0 Hz, 1H), 6.07 (d, J=3.0 Hz, 1H), 5.97 (d, J=15.6, 8.0 Hz, 1H), 3.86 (s, 2H), 3.71 (s, 3H), 3.37 (dd, J=8.0, 0.8 Hz, 2H), 3.19 (s, 2H), 3.15 (s, 6H), 2.29 (s, 3H).

EXAMPLE 2(8)

2-methyl-2-((2E)-3-(5-(5-methyl-2-(4-dimethylaminophenyl)oxazol-4-ylmethyl)furan-2-yl)-2-propenylthio)propanoic acid.ethyl ester

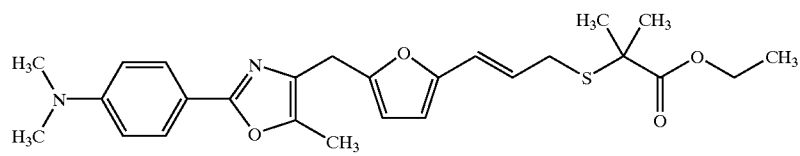

TLC: Rf 0.57 (hexane:ethyl acetate 2:1);

NMR (CDCl$_3$): δ 7.84 (m, 2H), 6.71 (m, 2H), 6.27 (d, J=15.8 Hz, 1H), 6.09 (d, J=3.4 Hz, 1H), 6.04 (d, J=3.4 Hz, 1H), 6.03 (m, 1H), 4.13 (q, J=7.2 Hz 2H), 3.85 (s, 2H), 3.40 (d, J=7.2 Hz, 2H), 3.01 (s, 6H), 2.26 (s, 3H), 1.53 (s, 6H), 1.25 (t, J=7.2 Hz, 3H).

EXAMPLE 2(9)

1-((2E)-3-(5-(5-methyl-2-(4-dimethylaminophenyl)oxazol-4-ylmethyl)furan-2-yl)-2-propenylthio)cyclobutanecarboxylic acid.ethyl ester

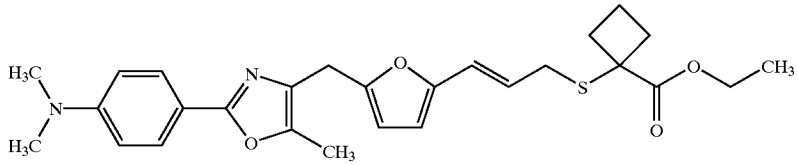

TLC: Rf 0.53 (hexane:ethyl acetate=2:1);

NMR (CDCl$_3$): δ 7.84 (m, 2H), 6.71 (m, 2H), 6.26 (d, J=15.8 Hz, 1H), 6.09 (d, J=3.2 Hz, 1H), 6.05 (m, 1H), 6.04 (d, J=3.2 Hz, 1H), 4.15 (q, J=7.2 Hz, 2H), 3.85 (s, 2H), 3.33 (d, J=7.0 Hz, 2H), 3.01 (s, 6H), 2.72–2.56 (m, 2H), 2.28–2.10 (m, 3H), 2.26 (s, 3H), 1.90 (m, 1H), 1.26 (t, J=7.2 Hz, 3H).

EXAMPLE 2(10)

2-methyl-2-((2E)-3-(5-(5-methyl-2-(4-dimethylaminopyridin-5-yl)oxazol-4-ylmethyl)furan-2-yl)-2-propenylthio)propanoic acid.ethyl ester

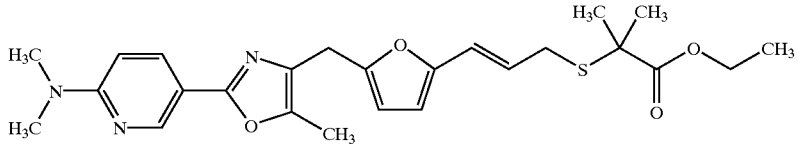

TLC: Rf 0.47 (hexane:ethyl acetate=1:1);

NMR (CDCl$_3$): δ 8.74 (dd, J=2.4, 0.8 Hz, 1H), 8.00 (dd, J=9.0, 2.4 Hz, 1H), 6.52 (dd, J=9.0, 0.8 Hz, 1H), 6.27 (d, J=15.6 Hz, 1H), 6.10 (d, J=3.2 Hz, 1H), 6.05 (d, J=3.2 Hz, 1H), 6.01 (d, J=15.6, 7.0 Hz, 1H), 4.13 (q, J=7.2 Hz, 2H), 3.84 (s, 2H), 3.41 (dd, J=7.0, 0.8 Hz, 2H), 3.14 (s, 6H), 2.27 (s, 3H), 1.53 (s, 6H), 1.26 (t, J=7.2 Hz, 3H).

EXAMPLE 2(11)

1-((2E)-3-(5-(5-methyl-2-(4-dimethylaminopyridin-5-yl)oxazol-4-ylmethyl)furan-2-yl)-2-propenylthio)cyclobutanecarboxylic acid.ethyl ester

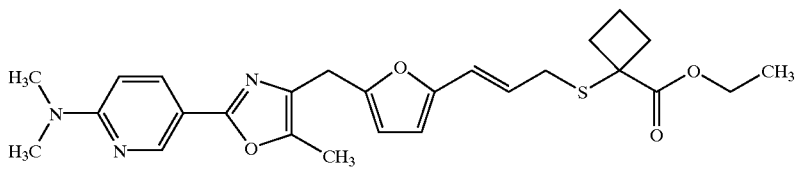

TLC: Rf 0.53 (hexane:ethyl acetate=1:1);

NMR (CDCl$_3$): δ 8.73 (dd, J=2.4, 0.8 Hz, 1H), 8.00 (dd, J=9.0, 2.4 Hz, 1H), 6.52 (dd, J=9.0, 0.8 Hz, 1H), 6.20 (d, J=15.8 Hz, 1H), 6.10 (d, J=3.0 Hz, 1H), 6.05 (d, J=3.0 Hz, 1H), 6.03 (d, J=15.8, 7.0 Hz, 1H), 4.16 (q, J=7.2 Hz, 2H), 3.84 (s, 2H), 3.33 (dd, J=7.0, 0.8 Hz, 2H), 3.14 (s, 6H), 2.70–2.53 (m, 2H), 2.36–2.04 (m, 6H), 1.96–1.70 (m, 1H), 1.26 (t, J=7.2 Hz, 3H).

EXAMPLE 3

2-((2E)-3-(5-(5-methyl-2-phenyloxazol-4-ylmethyl)furan-2-yl)-2-propenylthio)acetic acid

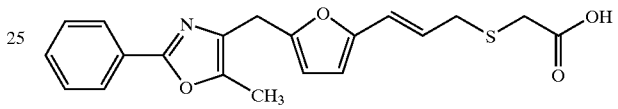

2N aqueous solution of sodium hydroxide (7.4 ml) was added to a solution of the compound prepared in Example 1 (1.88 g) in methanol (49 ml), and the resultant solution was stirred for 5 hours at room temperature. 2N hydrochloric acid (7.4 ml) was added to the reaction mixture, and the resultant solution was concentrated. The residue was crystallized from ethyl acetate to give the title compound (1.28 g) having the following physical data.

TLC: Rf 0.73 (chloroform:methanol=5:1);

NMR (CDCl$_3$): δ 7.96–8.01 (m, 2H), 7.39–7.46 (m, 3H), 6.26 (d, J=15.6 Hz, 1H), 6.14 (d, J=3.2 Hz, 1H), 6.06 (d, J=3.2 Hz, 1H), 6.01 (dt, J=15.6, 7.6 Hz, 1H), 3.90 (s, 2H), 3.38 (d, J=7.6 Hz, 2H), 3.21 (s, 2H), 2.33 (s, 3H).

EXAMPLE 3(1)~EXAMPLE 3(12)

The following compounds were obtained by the same procedure as Example 3, using compounds prepared in Example 2~Example 2(5).

EXAMPLE 3(1)

2-((2E)-3-(5-(5-methyl-2-(4-methylphenyl)oxazol-4-ylmethyl)furan-2-yl)-2-propenylthio)acetic acid

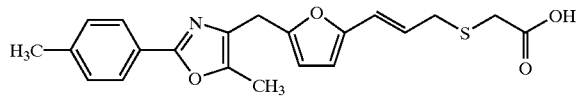

TLC: Rf 0.40 (chloroform:methanol=10:1);

NMR (CDCl$_3$): δ 7.87 (d, J=8.0 Hz, 2H), 7.23 (d, J=8.0 Hz, 2H), 6.25 (d, J=15.6 Hz, 1H), 6.13 (d, J=3.2 Hz, 1H), 6.05 (d, J=3.2 Hz, 1H), 6.00 (dt, J=15.6, 7.2 Hz, 1H), 3.89 (s, 2H), 3.37 (d, J=7.2 Hz, 2H), 3.20 (s, 2H), 2.38 (s, 3H), 2.31 (s, 3H).

EXAMPLE 3(2)

2-((2E)-3-(5-(5-methyl-2-(1,3-dioxaindan-5-yl)oxazol-4-ylmethyl)furan-2-yl)-2-propenylthio)acetic acid

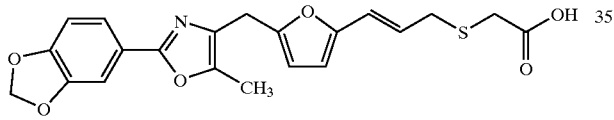

TLC: Rf 0.53 (chloroform:methanol=10:1);

NMR (CDCl$_3$): δ 7.53 (dd, J=8.0, 1.6 Hz, 1H), 7.44 (d, J=1.6 Hz, 1H), 6.85 (d, J=8.0 Hz, 1H), 6.25 (d, J=15.5 Hz, 1H), 6.14 (d, J=3.0 Hz, 1H), 6.09–5.92 (m, 4H), 3.87 (s, 2H), 3.38 (d, J=7.5 Hz, 2H), 3.20 (s, 2H), 2.30 (s, 3H).

EXAMPLE 3(3)

2-((2E)-3-(5-(5-methyl-2-(4-ethylphenyl)oxazol-4-ylmethyl)furan-2-yl)-2-propenylthio)acetic acid

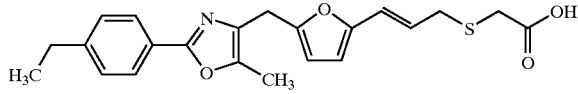

TLC: Rf 0.65 (chloroform:methanol=5:1);

NMR (CDCl$_3$): δ 7.89 (d, J=8.0 Hz, 2H), 7.25 (d, J=8.0 Hz, 2H), 6.25 (d, J=16.0 Hz, 1H), 6.13 (d, J=3.2 Hz, 1H), 6.05 (d, J=3.2 Hz, 1H), 6.00 (dt, J=16.0, 7.5 Hz, 1H), 3.90 (s, 2H), 3.37 (d, J=7.5 Hz, 2H), 3.20 (s, 2H), 2.68 (q, J=7.6 Hz, 2H), 2.32 (s, 3H), 1.25 (t, J=7.6 Hz, 3H).

EXAMPLE 3(4)

2-((2E)-3-(5-(5-methyl-2-phenyloxazol-4-ylmethyl)thiophen-2-yl)-2-propenylthio)acetic acid

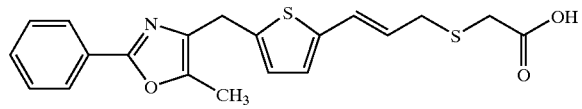

TLC: Rf 0.39 (chloroform:methanol=10:1);

NMR (CDCl$_3$): δ 8.00–7.97 (m, 2H), 7.44–7.40 (m, 3H), 6.74 (d, J=3.6 Hz, 1H), 6.73 (d, J=3.6 Hz, 1H), 6.52 (br.d, J=15.6 Hz, 1H), 5.84 (dt, J=15.6, 7.5 Hz, 1H), 4.02 (s, 2H), 3.35 (br.d, J=7.5 Hz, 2H), 3.18 (s, 2H), 2.34 (s, 3H).

EXAMPLE 3(5)

2-methyl-2-((2E)-3-(5-(5-methyl-2-(1,3-dioxaindan-5-yl)oxazol-4-ylmethyl)furan-2-yl)-2-propenylthio)propanoic acid

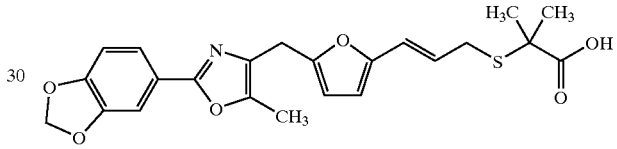

TLC: Rf 0.62 (water:methanol:chloroform=1:10:100);

NMR (CDCl$_3$): δ 7.53 (dd, J=8.0, 2.0 Hz, 1H), 7.44 (d, J=2.0 Hz, 1H), 6.84 (d, J=8.0 Hz, 1H), 6.28 (d, J=15.5 Hz, 1H), 6.09 (d, J=3.0 Hz, 1H), 6.06 (dt, J=15.5, 7.0 Hz, 1H), 6.03 (d, J=3.0 Hz, 1H), 6.00 (s, 2H), 3.86 (s, 2H), 3.43 (d, J=7.0 Hz, 2H), 2.27 (s, 3H), 1.54 (s, 6H).

EXAMPLE 3(6)

1-((2E)-3-(5-(5-methyl-2-(1,3-dioxaindan-5-yl)oxazol-4-ylmethyl)furan-2-yl)-2-propenylthio)cyclobutanecarboxylic acid

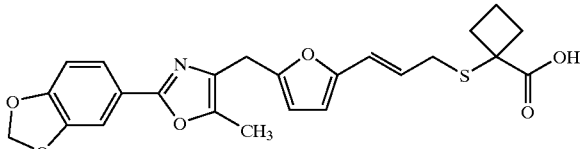

TLC: Rf 0.63 (water:methanol:chloroform=1:10:100);

NMR (CDCl$_3$): δ 7.52 (dd, J=8.0, 2.0 Hz, 1H), 7.44 (d, J=2.0 Hz, 1H), 6.84 (d, J=8.0 Hz, 1H), 6.26 (d, J=15.5 Hz, 1H), 6.09 (d, J=3.0 Hz, 1H), 6.07 (dt, J=15.5, 7.0 Hz, 1H), 6.03 (d, J=3.0 Hz, 1H), 6.00 (s, 2H), 3.86 (s, 2H), 3.36 (d, J=7.0 Hz, 2H), 2.68 (m, 2H), 2.40–1.80 (m, 4H), 2.27 (s, 3H).

EXAMPLE 3(7)

2-((2E)-3-(5-(5-methyl-2-(4-dimethylaminophenyl)oxazol-4-ylmethyl)furan-2-yl)-2-propenylthio)acetic acid

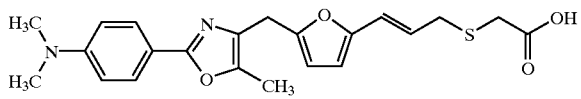

TLC: Rf 0.43 (chloroform:methanol=10:1);

NMR (CDCl$_3$ with 2 drops of CD$_3$OD): δ 7.83 (m, 2H), 6.71 (m, 2H), 6.26 (d, J=15.6 Hz, 1H), 6.13 (d, J=3.0 Hz, 1H), 6.04 (d, J=3.0 Hz, 1H), 6.02 (dt, J=15.6, 7.5 Hz, 1H), 3.85 (s, 2H), 3.37 (d, J=7.5 Hz, 2H), 3.18 (s, 2H), 3.01 (s, 6H), 2.29 (brs, 3H).

EXAMPLE 3(8)

2-((2E)-3-(5-(5-methyl-2-(2-dimethylaminopyridin-5-yl)oxazol-4-ylmethyl)furan-2-yl)-2-propenylthio)acetic acid

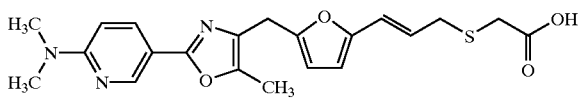

TLC: Rf 0.44 (chloroform:methanol=7:1);

NMR (CDCl$_3$): δ 8.73 (dd, J=2.4, 0.8 Hz, 1H), 7.99 (dd, J=9.0, 2.4 Hz, 1H), 6.53 (dd, J=9.0, 0.8 Hz, 1H), 6.27 (d, J=15.6 Hz, 1H), 6.13 (d, J=3.4 Hz, 1H), 6.06 (d, J=3.4 Hz, 1H), 5.99 (d, J=15.6, 7.2 Hz, 1H), 3.85 (s, 2H), 3.39 (d, J=7.2 Hz, 2H), 3.17 (s, 2H), 3.15 (s, 6H), 2.29 (s, 3H).

EXAMPLE 3(9)

2-methyl-2-((2E)-3-(5-(5-methyl-2-(4-dimethylaminophenyl)oxazol-4-ylmethyl)furan-2-yl)-2-propenylthio)propanoic acid

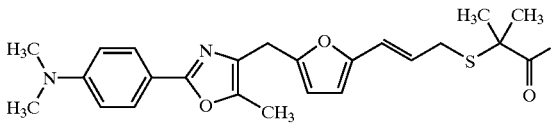

TLC: Rf 0.49 (chloroform:methanol=10:1);

NMR (CDCl$_3$): δ 7.84 (m, 2H), 6.70 (m, 2H), 6.26 (d, J=15.6 Hz, 1H), 6.08 (d, J=3.0 Hz, 1H), 6.06 (dt, J=15.6, 7.0 Hz, 1H), 6.01 (d, J=3.0 Hz, 1H), 3.86 (s, 2H), 3.40 (d, J=7.0 Hz, 2H), 3.01 (s, 6H), 2.27 (s, 3H), 1.54 (s, 6H),

EXAMPLE 3(10)

1-((2E)-3-(5-(5-methyl-2-(4-dimethylaminophenyl)oxazol-4-ylmethyl)furan-2-yl)-2-propenylthio)cyclobutanecarboxylic acid

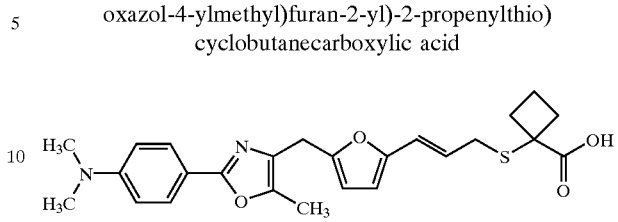

TLC: Rf 0.49 (chloroform:methanol=10:1);

NMR (CDCl$_3$): δ 7.85 (m, 2H), 6.70 (m, 2H), 6.24 (d, J=15.8 Hz, 1H), 6.09 (d, J=3.2 Hz, 1H), 6.07 (m, 1H), 6.02 (d, J=3.2 Hz, 1H), 3.87 (s, 2H), 3.33 (d, J=7.0 Hz, 2H), 3.01 (s, 6H), 2.78–2.56 (m, 2H), 2.30–2.08 (m, 3H), 2.27 (s, 3H), 2.02–1.80 (m, 1H).

EXAMPLE 3(11)

2-methyl-2-((2E)-3-(5-(5-methyl-2-(4-dimethylaminopyridin-5-yl)oxazol-4-ylmethyl)furan-2-yl)-2-propenylthio)propanoic acid

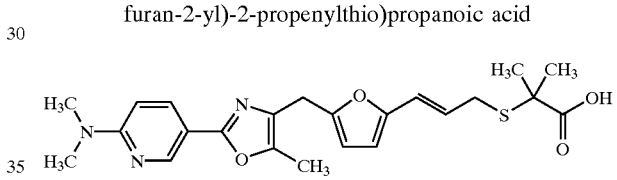

TLC: Rf 0.53 (chloroform:methanol=7:1);

NMR (CDCl$_3$): δ 8.74 (d, J=2.4 Hz, 1H), 8.01 (dd, J 9.0, 2.4 Hz, 1H), 6.52 (d, J=9.0 Hz, 1H), 6.26 (d, J=15.6 Hz, 1H), 6.15–5.98 (m, 3H), 3.85 (s, 2), 3.44 (d, J=7.2 Hz, 2H), 3.12 (s, 6H), 2.26 (s, 3H), 1.55 (s, 6H).

EXAMPLE 3(12)

1-((2E)-3-(5-(5-methyl-2-(4-dimethylaminopyridin-5-yl)oxazol-4-ylmethyl)furan-2-yl)-2-propenylthio)cyclobutanecarboxylic acid

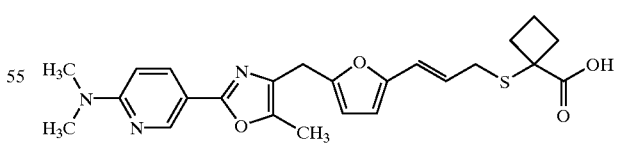

TLC: Rf 0.54 (chloroform:methanol=7:1);

NMR (CDCl$_3$): δ 8.74 (d, J=2.4 Hz, 1H), 8.02 (dd, J=9.0, 2.4 Hz, 1H), 6.52 (d, J=9.0 Hz, 1H), 6.26 (d, J=15.6 Hz, 1H), 6.17–6.00 (m, 3H), 3.85 (s, 2H), 3.36 (d, J=7.0 Hz, 2H), 3.13 (s, 6H), 2.82–2.56 (m, 2H), 2.35–2.10 (m, 6H), 2.02–1.77 (m, 1H).

EXAMPLE 4

2-((2E)-3-(5-(5-methyl-2-(1,3-dioxaindan-5-yl)oxazol-4-ylmethyl)furan-2-yl)-2-propenylsulfinyl)acetic acid

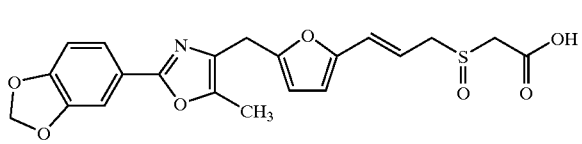

A aqueous solution (100 ml) of OXONE (trade mark) (891 mg) was added dropwise to a solution of the compound prepared in Example 3(2) (1.0 g) in tetrahydrofuran (200 ml) over a period of 30 minutes at −2~−3° C., and the resultant solution was stirred for 10 minutes at 0° C. Ice water was added to the reaction solution, and the resultant solution was extracted with ethyl acetate, and the extract was washed with water and a saturated aqueous solution of sodium chloride, dried over anhydrous magnesium sulfate, and concentrated. The residue was purified by silica gel column chromatography (chloroform:methanol=50:1→10:1) to give the title compound (750 mg) having the following physical data.

TLC: Rf 0.24 (water:methanol:chloroform=1:10:50);

NMR (CDCl$_3$): δ 7.52 (dd, J=8.0, 1.5 Hz, 1H), 7.43 (d, J=1.5 Hz, 1H), 6.85 (d, J=8.0 Hz, 1H), 6.45 (d, J=15.5 Hz, 1H), 6.22 (d, J=3.5 Hz, 1H), 6.05 (d, J=3.5 Hz, 1H), 6.04 (dt, J=15.5, 8.0 Hz, 1H), 6.01 (s, 2H), 3.88 (s, 2H), 3.85–3.75 (m, 2H), 3.81 (d, J=14.5 Hz, 1H), 3.66 (d, J=14.5 Hz, 1H), 2.31 (s, 3H).

EXAMPLE 4(1)

2-((2E)-3-(5-(5-methyl-2-phenyloxazol-4-ylmethyl)furan-2-yl)-2-propenylsulfinyl)acetic acid

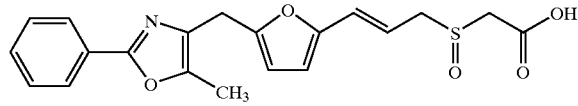

The compound having the following physical data was obtained by the same procedure as Example 4, using the compound prepared in Example 3.

TLC: Rf 0.11 (water:methanol:chloroform=1:10:50);

NMR (CDCl$_3$): δ 9.30 (br., 1H), 7.98 (m, 2H), 7.50–7.35 (m, 3H), 6.45 (d, J=15.5 Hz, 1H), 6.21 (d, J=3.0 Hz, 1H), 6.06 (d, J=3.0 Hz, 1H), 6.05 (dt, J=15.5, 8.0 Hz, 1H), 3.91 (s, 2H), 3.85 (dd, J=12.5, 8.0 Hz, 1H), 3.82 (d, J=14.0 Hz, 1H), 3.73 (dd, J=12.5, 8.0 Hz, 1H), 3.68 (d, J=14.0 Hz, 1H), 2.33 (s, 3H).

EXAMPLE 5

2-((2E)-3-(5-(5-methyl-2-(1,3-dioxaindan-5-yl)oxazol-4-ylmethyl)furan-2-yl)-2-propenylsulfonyl)acetic acid

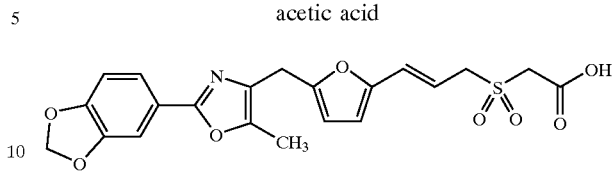

A aqueous solution (5 ml) of OXONE (trade mark) (864 mg) was added to a solution of the compound prepared in Example 4 (503 mg) in tetrahydrofuran (10 ml) at 0° C., and the resultant solution was stirred for 4 hours at room temperature. Cold water was added to the reaction solution, and the resultant solution was extracted with ethyl acetate, and the extract was washed with water and a saturated aqueous solution of sodium chloride, dried over anhydrous magnesium sulfate, and concentrated. The residue was washed with a mixed solution of chloroform/methanol (20:1) to give the title compound (350 mg) having the following physical data.

TLC: Rf 0.61 (chloroform:methanol:acetic acid= 50:20:1);

NMR (CD$_3$OD+10 drops of CDCl$_3$): δ 7.49 (dd, J=8.0, 1.6 Hz, 1H), 7.37 (d, J=1.6 Hz, 1H), 6.89 (d, J=8.0 Hz, 1H), 6.58 (d, J=15.6 Hz, 1H), 6.32 (d, J=3.2 Hz, 1H), 6.12 (d, J=3.2 Hz, 1H ), 5.96–6.14 (m, 3H), 4.14 (d, J=7.8 Hz, 2H), 4.08 (s, 2H), 3.88 (s, 2H), 2.32 (s, 3H).

EXAMPLE 5(1)

2-((2E)-3-(5-(5-methyl-2-phenyloxazol-4-ylmethyl)furan-2-yl)-2-propenylsulfonyl)acetic acid

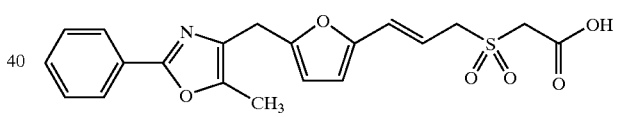

The compound having the following physical data was obtained by the same procedure as Example 5, using the compound prepared in Example 4(1).

TLC: Rf 0.34 (water:methanol:chloroform=1:10:50);

NMR (DMSO-d6): δ 7.91 (m, 2H), 7.60–7.40 (m, 3H), 6.58 (d, J=15.5 Hz, 1H), 6.43 (d, J=3.0 Hz, 1H), 6.19 (d, J=3.0 Hz, 1H), 5.95 (m, 1H), 4.24 (m, 2H), 3.95 (m, 2H), 3.92 (s, 2H), 2.35 (s, 3H).

Reference Example 7

2-(5-methyl-2-phenyloxazol-4-ylmethyl)furan

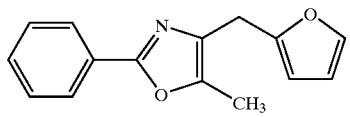

The title compound (5.27 g) having the following physical data was obtained by the same procedure as Reference Example 4, using 4-chloromethyl-5-methyl-2-phenyloxazole (8.31 g) and 2-(n-butylstannyl)furan (15.7 g).

TLC: Rf 0.68 (ethyl acetate:hexane=1:4);

NMR (CDCl₃): δ 8.02–7.97 (m, 2H), 7.44–7.40 (m, 3H), 7.35–7.34 (m, 1H), 6.32–6.30 (m, 1H), 6.12–6.10 (m, 1H), 3.91 (s, 2H), 2.29 (s, 3H).

Reference Example 8

2-bromo-5-(5-methyl-2-phenyloxazol-4-ylmethyl) furan

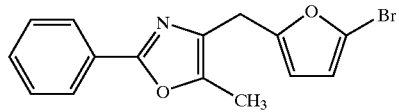

N-bromosuccinimide (2.8 g) and 2,2'-azobisisobutyronitrile (10 mg) were added to a solution of the compound prepared in Reference Example 7 (2.0 g) in benzene (40 ml), and the resultant solution was stirred for 5 hours at room temperature. The insoluble material in the reaction solution was filtered out. The filtrate was diluted with ethyl acetate, and the resultant solution was washed with a saturated aqueous solution of sodium hydrogencarbonate and a saturated aqueous solution of sodium chloride, dried over anhydrous magnesium sulfate, and concentrated. The residue was purified by silica gel column chromatography (ethyl acetate:hexane=1:20) to give the title compound (267 mg) having the following physical data.

TLC: Rf 0.68 (ethyl acetate:toluene=1:4);

NMR (CDCl₃): δ 8.01–7.96 (m, 2H), 7.45–7.40(m, 3H), 6.21 (d, J=3.2 Hz, 1H), 3.87 (br.s, 2H), 2.31 (s, 3H).

Reference Example 9

3-(5-(5-methyl-2-phenyloxazol-4-ylmethyl)furan-2-yl)-2-propyn-1-ol

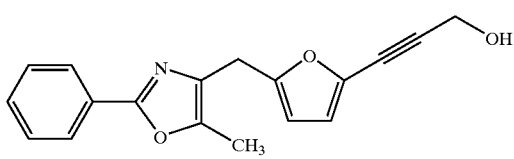

The mixture of the compound prepared in Reference Example 8 (260 mg), propargyl alcohol (94 μl), tetrakis(triphenylphosphine)palladium (47 mg), copper bromide (20 mg), lithium bromide (70 mg) and piperidine (1 ml) was stirred for 30 minutes at 90° C. After cooling to room temperature, the reaction mixture was concentrated. The residue was purified by silica gel column chromatography (ethyl acetate:hexane=1:2) to give the title compound (126 mg) having the following physical data.

TLC: Rf 0.46 (ethyl acetate:hexane=1:1);

NMR (CDCl₃): δ 8.01–7.96 (m, 2H), 7.45–7.40(m, 3H), 6.63 (d, J=3.2 Hz, 1H), 6.10 (d, J=3.2 Hz, 1H), 4.50 (s, 2H), 3.88 (s, 2H), 2.30 (s, 3H).

EXAMPLE 6

2-(3-(5-(5-methyl-2-phenyloxazol-4-ylmethyl)furan-2-yl)-2-propynylthio)acetic acid.methyl ester

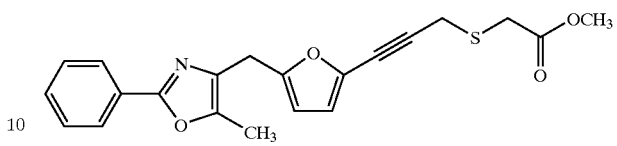

The title compound having the following physical data was obtained by the same procedure as Reference Example 9, using the compound prepared in Example 9.

TLC: Rf 0.35 (ethyl acetate:hexane=1:3);

NMR (CDCl₃): δ8.01–7.96 (m, 2H), 7.44–7.40 (m, 3H), 6.49 (d, J=3.4 Hz, 1H), 6.10–6.08 (m, 1H), 3.88 (br.s, 1H), 3.74 (s, 3H), 3.65 (s, 2H), 3.45 (s, 2H), 2.31 (s, 3H).

EXAMPLE 7

2-(3-(5-(5-methyl-2-phenyloxazol-4-ylmethyl)furan-2-yl)-2-propynylthio)acetic acid

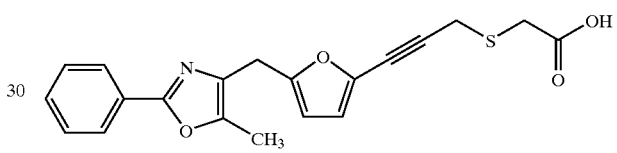

The title compound having the following physical data was obtained by the same procedure as Reference Example 3, using the compound prepared in Example 6.

TLC: Rf 0.25 (chloroform:methanol=10:1);

NMR (CDCl₃): δ 8.30–7.90 (br.s, 1H), 7.98–7.95 (m, 2H), 7.45–7.39 (m, 3H), 6.48 (d, J=3.3 Hz, 1H), 6.08 (d, J=3.3 Hz, 1H), 3.89 (s, 2H), 3.65 (s, 2H), 3.46 (s, 2H), 2.30 (s, 3H).

FORMULATION EXAMPLE

Formulation Example 1

The following compounds were admixed in conventional method and punched out to obtain 100 tablets each containing 100 mg of active ingredient.

| | |
|---|---|
| 2-((2E)-3-(5-(5-methyl-2-phenyloxazol-4-ylmethyl)furan-2-yl)-2-propenylthio)acetic acid | 10.0 g |
| Cellulose calcium glycolate (disintegrating agent) | 0.2 g |
| Magnesium stearate (lubricating agent) | 0.1 g |
| Micro crystalline cellulose | 9.7 g |

Formulation Example 2

The following components were admixed in a conventional method, and the solution was sterilized in a conventional method, placed 5 ml portions into ampoules and freeze-dried in a conventional method to obtain 100 ampoules each containing 20 mg of active ingredient

| | |
|---|---|
| 2-((2E)-3-(5-(5-methyl-2-phenyloxazol-4-ylmethyl)furan-2-yl)-2-propenylthio)acetic acid | 2.0 g |
| Mannit | 5.0 g |
| Distilled water | 500 ml |

What is claimed is:

1. A compound of formula (I)

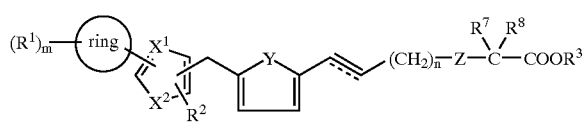

wherein

R$^1$ independently, is hydrogen, C1~8 alkyl, halogen, C1~4 alkoxy, C1~4 alkylthio, nitro, NR$^4$R$^{5'}$ in which R$^4$ and R$^5$ each independently, is C1~4 alkyl, cyano, trifluoromethyl, trifluoromethyloxy, or carbocyclic ring wherein the carbocyclic ring is optionally substituted by a group selected from C1~4 alkyl, C1~4 alkoxy, halogen or trifluoromethyl, R$^2$ is hydrogen, C1~8 alkyl, halogen, C1~4 alkoxy, C1~4 alkylthio, nitro, NR$^4$R$^5$, in which R$^4$ and R$^5$ each independently, is C1~4 alkyl, cyano, trifluoromethyl or trifluoromethyloxy, R$^3$ is hydrogen or C1~4 alkyl, X$^1$ is —N—, X$^2$ and Y each independently, is —O—, or —S—, Z is —O— or —S(O)$_p$— in which p is 0, 1 or 2, R$^7$ and R$^8$ each independently, is hydrogen or C1~4 alkyl, or R$^7$ and R$^8$ taken together with carbon atom to which is attached represents C3~7 cycloalkylene,

is carbocyclic ring,

═══ is double bond or triple bond, m and n each independently, is 1~3, a non-toxic salt thereof, or hydrate thereof.

2. A compound according to claim 1, wherein $$\overline{\overline{\phantom{xxx}}}$$

is double bond, a non-toxic salt thereof, or a hydrate thereof.

3. A compound according to claim 1, wherein $X^1$ is —N—, $X^2$ is —O—, Y is —O—, $$\overline{\overline{\phantom{xxx}}}$$

is double bond a non-toxic salt thereof, or a hydrate thereof.

4. A compound according to claim 1, which is (1) 2-((2E)-3-(5-(5-methyl-2-phenyloxazol-4-ylmethyl)furan-2-yl)-2-propenylthio)acetic acid.ethyl ester, (2) 2-((2E)-3-(5-(5-methyl-2-(4-methylphenyl)oxazol-4-ylmethyl)furan-2-yl)-2-propenylthio)acetic acid.methyl ester, (3) 2-((2E)-3-(5-(5-methyl-2-(4-ethylphenyl)oxazol-4-ylmethyl)furan-2-yl)-2-propenylthio)acetic acid.methyl ester, (4) 2-((2E)-3-(5-(5-methyl-2-phenyloxazol-4-ylmethyl)thiophen-2-yl)-2-propenylthio)acetic acid.methyl ester, (5) 2-((2E)-3-(5-(5-methyl-2-(4-dimethylaminophenyl)oxazol-4-ylmethyl)furan-2-yl)-2-propenylthio)acetic acid.methyl ester, (6) 2-methyl-2-((2E)-3-(5-(5-methyl-2-(4-dimethylaminophenyl)oxazol-4-ylmethyl)furan-2-yl)-2-propenylthio)propanoic acid.ethyl ester (7) 1-((2E)-3-(5-(5-methyl-2-(4-dimethylaminophenyl)oxazol-4-ylmethyl)furan-2-yl)-2-propenylthio)cyclobutanecarboxylic acid.ethyl ester (8) 2-((2E)-3-(5-(5-methyl-2-phenyloxazol-4-ylmethyl)furan-2-yl)-2-propenylthio)acetic acid, (9) 2-((2E)-3-(5-(5-methyl-2-(4-methylphenyl)oxazol-4-ylmethyl)furan-2-yl)-2-propenylthio)acetic acid,

(10) 2-((2E)-3-(5-(5-methyl-2-(4-ethylphenyl)oxazol-4-ylmethyl)furan-2-yl)-2-propenylthio)acetic acid,

(11) 2-((2E)-3-(5-(5-methyl-2-phenyloxazol-4-ylmethyl)thiophen-2-yl)-2-propenylthio)acetic acid,

(12) 2-((2E)-3-(5-(5-methyl-2-(4-dimethylaminophenyl)oxazol-4-ylmethyl)furan-2-yl)-propenylthio)acetic acid,

(13) 2-methyl-2-((2E)-3-(5-(5-methyl-2-(4-dimethylaminophenyl)oxazol-4-ylmethyl)furan-2-yl)-2-propenylthio)propanoic acid,

(14) 1-((2E)-3-(5-(5-methyl-2-(4-dimethylaminophenyl)oxazol-4-ylmethyl)furan-2-yl)-2-propenylthio)cyclobutanecarboxylic acid,

(15) 2-((2E)-3-(5-(5-methyl-2-phenyloxazol-4-ylmethyl)furan-2-yl)-2-propenylsulfinyl)acetic acid,

(16) 2-((2E)-3-(5-(5-methyl-2-phenyloxazol-4-ylmethyl)furan-2-yl)-2-propenylsulfonyl)acetic acid,

(17) 2-(3-(5-(5-methyl-2-phenyloxazol-4-ylmethyl)furan-2-yl)-2-propynylthio)acetic acid.methyl ester, or

(18) 2-(3-(5-(5-methyl-2-phenyloxazol-4-ylmethyl)furan-2-yl)-2-propynylthio)acetic acid, or a non-toxic salt thereof, or a hydrate thereof.

5. A pharmaceutical composition comprising a compound of formula (I) according to claim 1, a non-toxic salt thereof or a hydrate thereof, as an active ingredient, and a pharmaceutically acceptable carrier.

6. A method of treating diseases associated with metabolic disorders selected from the group consisting of diabetes, obesity, syndrome X, hypercholesterolemia and hyperlipoproteinemia comprising administering to a subject in need thereof an effective amount of a composition according to claim 5.

\* \* \* \* \*

UNITED STATES PATENT AND TRADEMARK OFFICE
CERTIFICATE OF CORRECTION

PATENT NO.     : 6,589,969 B1
DATED          : July 8, 2003
INVENTOR(S)    : Hisao Tajima, Yoshisuke Nakayama and Daikichi Fukushima It is certified that error appears in the above-identified patent and that said Letters Patent is hereby corrected as shown below:

Column 1,
Line 22, delete "PCT Filed: Aug. 9, 1999" insert -- PCT Filed: Sep 8, 1999 --

Signed and Sealed this

Third Day of February, 2004

JON W. DUDAS
*Acting Director of the United States Patent and Trademark Office*